US009204974B2

(12) United States Patent
Glerum et al.

(10) Patent No.: US 9,204,974 B2
(45) Date of Patent: *Dec. 8, 2015

(54) EXPANDABLE FUSION DEVICE AND METHOD OF INSTALLATION THEREOF

(71) Applicant: Globus Medical Inc., Audubon, PA (US)

(72) Inventors: Chad Glerum, Pennsburg, PA (US); Sean Suh, Jamesburg, NJ (US); Mark Weiman, Coatesville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/499,815

(22) Filed: Sep. 29, 2014

(65) Prior Publication Data

US 2015/0051703 A1     Feb. 19, 2015

Related U.S. Application Data

(63) Continuation of application No. 13/948,915, filed on Jul. 23, 2013, now Pat. No. 8,888,853, which is a continuation of application No. 13/451,097, filed on Apr. 19, 2012, now Pat. No. 8,556,979, which is a continuation of application No. 13/440,158, filed on Apr. 5, 2012, now Pat. No. 8,679,183, which is a continuation-in-part of application No. 13/273,994, filed on Oct. 14, 2011, which is a continuation-in-part of application No. 12/823,736, filed on Jun. 25, 2010, now Pat. No. 8,685,098, which is a continuation of application No. 12/579,833, filed on Oct. 15, 2009, now Pat. No. 8,062,375.

(51) Int. Cl.
*A61F 2/44* (2006.01)
*A61F 2/46* (2006.01)
*A61F 2/30* (2006.01)

(52) U.S. Cl.
CPC ............... *A61F 2/4455* (2013.01); *A61F 2/447* (2013.01); *A61F 2/4684* (2013.01); *A61F 2002/3021* (2013.01); *A61F 2002/3052* (2013.01); *A61F 2002/3055* (2013.01); *A61F 2002/30207* (2013.01); *A61F 2002/30265* (2013.01); *A61F 2002/30365* (2013.01); *A61F 2002/30367* (2013.01); *A61F 2002/30372* (2013.01); *A61F 2002/30373* (2013.01); *A61F 2002/30387* (2013.01); *A61F 2002/30482* (2013.01); *A61F 2002/30484* (2013.01); *A61F 2002/30492* (2013.01); *A61F 2002/30495* (2013.01);

(Continued)

(58) Field of Classification Search
USPC ......... 623/17.11–17.16; 411/75, 80; 403/297, 403/373–374.4; 254/11
See application file for complete search history.

(56) References Cited

U.S. PATENT DOCUMENTS 4,349,921 A    9/1982 Kuntz
4,599,086 A    7/1986 Doty
(Continued)

FOREIGN PATENT DOCUMENTS

DE    4012622 C1    7/1991
DE    4327054 C1    4/1995
(Continued)

*Primary Examiner* — Anu Ramana
*Assistant Examiner* — Jessica Weiss

(57) ABSTRACT

The present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate, the first and second endplates capable of being moved in a direction away from the body portion into an expanded configuration or capable of being moved towards the body portion into an unexpanded configuration. The fusion device is capable of being deployed and installed in both configurations.

20 Claims, 32 Drawing Sheets

(52) U.S. Cl.
CPC ............... *A61F2002/30507* (2013.01); *A61F 2002/30517* (2013.01); *A61F 2002/30523* (2013.01); *A61F 2002/30551* (2013.01); *A61F 2002/30556* (2013.01); *A61F 2002/30578* (2013.01); *A61F 2002/30579* (2013.01); *A61F 2002/30596* (2013.01); *A61F 2002/30598* (2013.01); *A61F 2002/30601* (2013.01); *A61F 2002/30841* (2013.01); *A61F 2002/30904* (2013.01); *A61F 2002/4475* (2013.01); *A61F 2250/0004* (2013.01); *A61F 2310/00017* (2013.01); *A61F 2310/00023* (2013.01); *A61F 2310/00179* (2013.01)

(56) References Cited

U.S. PATENT DOCUMENTS

| | | | |
|---|---|---|---|
| 4,863,476 A | 9/1989 | Shepperd | |
| 4,863,477 A | 9/1989 | Monson | |
| 5,123,926 A | 6/1992 | Pisharodi | |
| 5,290,312 A | 3/1994 | Kojimoto et al. | |
| 5,306,310 A | 4/1994 | Siebels | |
| 5,375,823 A | 12/1994 | Navas | |
| 5,390,683 A | 2/1995 | Pisharodi | |
| 5,522,899 A | 6/1996 | Michelson | |
| 5,534,030 A | 7/1996 | Navarro et al. | |
| 5,554,191 A | 9/1996 | Lahille et al. | |
| 5,571,192 A | 11/1996 | Schonhoffer | |
| 5,645,596 A | 7/1997 | Kim | |
| 5,653,763 A | 8/1997 | Errico et al. | |
| 5,665,122 A | 9/1997 | Kambin | |
| 5,676,701 A | 10/1997 | Yuan et al. | |
| 5,865,848 A * | 2/1999 | Baker | 623/17.15 |
| 6,039,761 A | 3/2000 | Li et al. | |
| 6,045,579 A | 4/2000 | Hochshuler et al. | |
| 6,080,193 A | 6/2000 | Hochshuler | |
| 6,099,531 A | 8/2000 | Bonutti | |
| 6,126,689 A | 10/2000 | Brett | |
| 6,176,882 B1 * | 1/2001 | Biedermann et al. | 623/17.15 |
| 6,258,125 B1 | 7/2001 | Paul et al. | |
| 6,554,863 B2 | 4/2003 | Paul et al. | |
| 6,558,423 B1 | 5/2003 | Michelson | |
| 6,562,074 B2 | 5/2003 | Gerbec et al. | |
| 6,576,016 B1 | 6/2003 | Hochshuler et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,692,495 B1 | 2/2004 | Zacouto | |
| 6,706,070 B1 | 3/2004 | Wagner et al. | |
| 6,752,832 B2 | 6/2004 | Neumann | |
| 6,814,756 B1 | 11/2004 | Michelson | |
| 6,830,589 B2 | 12/2004 | Erickson | |
| 6,849,093 B2 | 2/2005 | Michelson | |
| 6,852,129 B2 | 2/2005 | Gerbec et al. | |
| 6,863,673 B2 | 3/2005 | Gerbec et al. | |
| 6,881,228 B2 | 4/2005 | Zdeblick et al. | |
| 7,018,415 B1 | 3/2006 | McKay | |
| 7,070,598 B2 | 7/2006 | Lim et al. | |
| 7,204,853 B2 | 4/2007 | Gordon | |
| 7,217,291 B2 | 5/2007 | Zucherman et al. | |
| 7,282,063 B2 | 10/2007 | Cohen et al. | |
| 7,316,714 B2 | 1/2008 | Gordon | |
| 7,473,276 B2 | 1/2009 | Aebi et al. | |
| 7,547,325 B2 | 6/2009 | Biedermann et al. | |
| 7,621,953 B2 | 11/2009 | Braddock, Jr. et al. | |
| 7,641,693 B2 | 1/2010 | Gutlin et al. | |
| 7,682,396 B2 | 3/2010 | Beaurain et al. | |
| 7,749,270 B2 | 7/2010 | Peterman | |
| 7,753,958 B2 | 7/2010 | Gordon | |
| 7,771,473 B2 | 8/2010 | Thramann | |
| 7,780,732 B2 | 8/2010 | Abernathie | |
| 7,799,081 B2 | 9/2010 | McKinley | |
| 7,815,683 B2 | 10/2010 | Melkent et al. | |
| 7,837,734 B2 | 11/2010 | Zucherman et al. | |
| 7,875,078 B2 | 1/2011 | Wysocki et al. | |
| 7,901,409 B2 | 3/2011 | Canaveral et al. | |
| 7,909,869 B2 | 3/2011 | Gordon | |
| 7,951,199 B2 | 5/2011 | Miller | |
| 8,062,375 B2 | 11/2011 | Glerum | |
| 8,105,358 B2 * | 1/2012 | Phan | 606/249 |
| 8,123,810 B2 | 2/2012 | Gordon | |
| 8,137,405 B2 | 3/2012 | Kostuik | |
| 8,647,386 B2 | 2/2014 | Gordon | |
| 2002/0045945 A1 | 4/2002 | Liu | |
| 2002/0068976 A1 | 6/2002 | Jackson | |
| 2002/0068977 A1 | 6/2002 | Jackson | |
| 2004/0030387 A1 | 2/2004 | Landry | |
| 2004/0049271 A1 | 3/2004 | Biedermann | |
| 2004/0054412 A1 | 3/2004 | Gerbec et al. | |
| 2004/0153065 A1 | 8/2004 | Lim | |
| 2005/0021041 A1 | 1/2005 | Michelson | |
| 2005/0021145 A1 | 1/2005 | de Villiers | |
| 2005/0033432 A1 | 2/2005 | Gordon | |
| 2005/0080422 A1 | 4/2005 | Otte | |
| 2005/0113916 A1 | 5/2005 | Branch, Jr. | |
| 2005/0149188 A1 | 7/2005 | Cook | |
| 2005/0171541 A1 | 8/2005 | Boehm | |
| 2005/0251258 A1 | 11/2005 | Jackson | |
| 2005/0273171 A1 | 12/2005 | Gordon | |
| 2005/0273174 A1 | 12/2005 | Gordon | |
| 2005/0278026 A1 | 12/2005 | Gordon | |
| 2005/0283244 A1 | 12/2005 | Gordon | |
| 2005/0283245 A1 | 12/2005 | Gordon | |
| 2006/0004453 A1 | 1/2006 | Bartish, Jr. et al. | |
| 2006/0015184 A1 | 1/2006 | Winterbottom | |
| 2006/0058878 A1 | 3/2006 | Michelson | |
| 2006/0084986 A1 | 4/2006 | Grinberg | |
| 2006/0122701 A1 | 6/2006 | Kister | |
| 2006/0129244 A1 | 6/2006 | Ensign | |
| 2006/0142859 A1 | 6/2006 | McLuen | |
| 2006/0149385 A1 | 7/2006 | McKay | |
| 2006/0195192 A1 | 8/2006 | Gordon et al. | |
| 2006/0229729 A1 | 10/2006 | Gordon | |
| 2006/0241770 A1 | 10/2006 | Rhoda | |
| 2006/0253201 A1 | 11/2006 | Mcluen | |
| 2007/0043442 A1 | 2/2007 | Abernathie | |
| 2007/0050030 A1 | 3/2007 | Kim | |
| 2007/0050032 A1 | 3/2007 | Gittings et al. | |
| 2007/0055377 A1 | 3/2007 | Hanson et al. | |
| 2007/0191951 A1 | 8/2007 | Branch | |
| 2007/0255415 A1 | 11/2007 | Edie et al. | |
| 2007/0270963 A1 | 11/2007 | Melkent et al. | |
| 2007/0270968 A1 | 11/2007 | Baynham | |
| 2008/0021559 A1 | 1/2008 | Thramann | |
| 2008/0065222 A1 | 3/2008 | Hamada | |
| 2008/0114467 A1 | 5/2008 | Capote | |
| 2008/0140207 A1 * | 6/2008 | Olmos et al. | 623/17.16 |
| 2008/0147194 A1 | 6/2008 | Grotz | |
| 2008/0167657 A1 | 7/2008 | Greenhalgh | |
| 2008/0183204 A1 | 7/2008 | Greenhalgh et al. | |
| 2008/0221694 A1 | 9/2008 | Warnick | |
| 2008/0275455 A1 | 11/2008 | Berry et al. | |
| 2008/0281346 A1 | 11/2008 | Greenhalgh et al. | |
| 2008/0288073 A1 | 11/2008 | Renganath et al. | |
| 2008/0300598 A1 | 12/2008 | Barreiro et al. | |
| 2008/0306488 A1 | 12/2008 | Altarac et al. | |
| 2008/0319487 A1 * | 12/2008 | Fielding et al. | 606/263 |
| 2008/0319549 A1 | 12/2008 | Greenhalgh et al. | |
| 2009/0024217 A1 | 1/2009 | Levy | |
| 2009/0076616 A1 | 3/2009 | Duggal | |
| 2009/0125062 A1 | 5/2009 | Arnin | |
| 2009/0149956 A1 | 6/2009 | Greenhalgh et al. | |
| 2009/0149959 A1 | 6/2009 | Conner et al. | |
| 2009/0204218 A1 | 8/2009 | Richelsoph | |
| 2009/0222100 A1 | 9/2009 | Cipoletti et al. | |
| 2009/0240334 A1 | 9/2009 | Richelsoph | |
| 2009/0270989 A1 | 10/2009 | Conner et al. | |
| 2009/0281628 A1 | 11/2009 | Oglaza | |
| 2009/0292361 A1 | 11/2009 | Lopez | |
| 2009/0299478 A1 | 12/2009 | Carls et al. | |
| 2009/0312763 A1 | 12/2009 | Mccormack | |
| 2010/0049324 A1 | 2/2010 | Valdevit | |
| 2010/0070041 A1 | 3/2010 | Peterman | |
| 2010/0082109 A1 | 4/2010 | Greenhalgh et al. | |

(56) References Cited

U.S. PATENT DOCUMENTS

| | | |
|---|---|---|
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0265309 A1 | 10/2012 | Glerum |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0158669 A1 | 6/2013 | Sungarian |

FOREIGN PATENT DOCUMENTS

| | | |
|---|---|---|
| EP | 0576379 B1 | 6/1993 |
| EP | 0610837 B1 | 7/1994 |
| FR | 2794968 | 12/2000 |
| JP | 2000-513263 | 10/2000 |
| SU | 1424826 A1 | 9/1988 |
| WO | 9201428 A1 | 2/1992 |
| WO | 9525485 A1 | 9/1995 |
| WO | 9942062 A1 | 8/1999 |
| WO | 9966867 A1 | 12/1999 |
| WO | 0245625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |

\* cited by examiner

EXPANDABLE FUSION DEVICE AND METHOD OF INSTALLATION THEREOF

FIELD OF THE INVENTION

This Patent Application is a continuation of U.S. patent application Ser. No. 13/948,915 which is a continuation of U.S. patent application Ser. No. 13/451,097 which is a continuation application claiming priority to U.S. patent application Ser. No. 13/440,158, filed Apr. 5, 2012, which is a continuation-in-part application of U.S. patent application Ser. No. 12/823,736, filed Jun. 25, 2010, and a continuation-in-part application claiming priority to U.S. patent application Ser. No. 13/273,994, filed Oct. 14, 2011, which is a continuation of U.S. patent application Ser. No. 12/579,833, filed Oct. 15, 2009, now issued as U.S. Pat. No. 8,062,375, the entire contents of which are incorporated by reference.

FIELD OF THE INVENTION

The present invention relates to the apparatus and method for promoting an intervertebral fusion, and more particularly relates to an expandable fusion device capable of being inserted between adjacent vertebrae to facilitate the fusion process.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In an exemplary embodiment, the present invention provides an expandable fusion device capable of being installed inside an intervertebral disc space to maintain normal disc spacing and restore spinal stability, thereby facilitating an intervertebral fusion. In one embodiment, the fusion device includes a body portion, a first endplate, and a second endplate. The first and second endplates are capable of being moved in a direction away from the body portion into an expanded configuration or capable of being moved towards the body portion into an unexpanded configuration. The expandable fusion device is capable of being deployed and installed in the unexpanded configuration or the expanded configuration.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
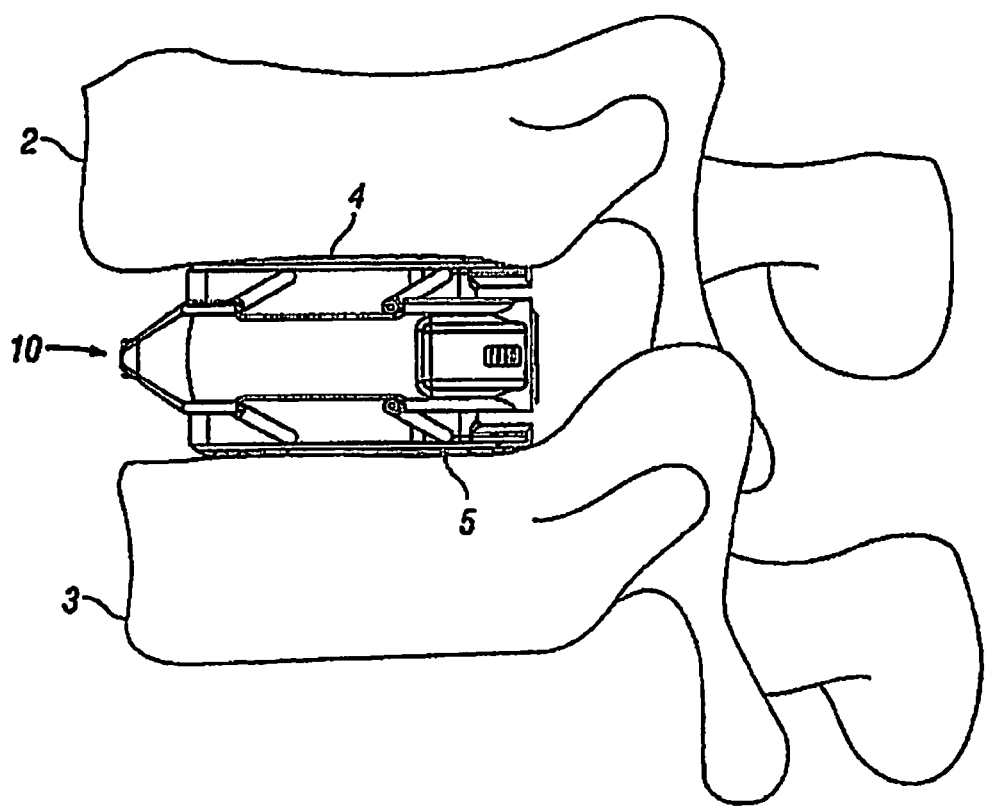
FIG. 1 is a side view of an embodiment of an expandable fusion device shown between adjacent vertebrae according to the present invention.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device.

Figure 2:
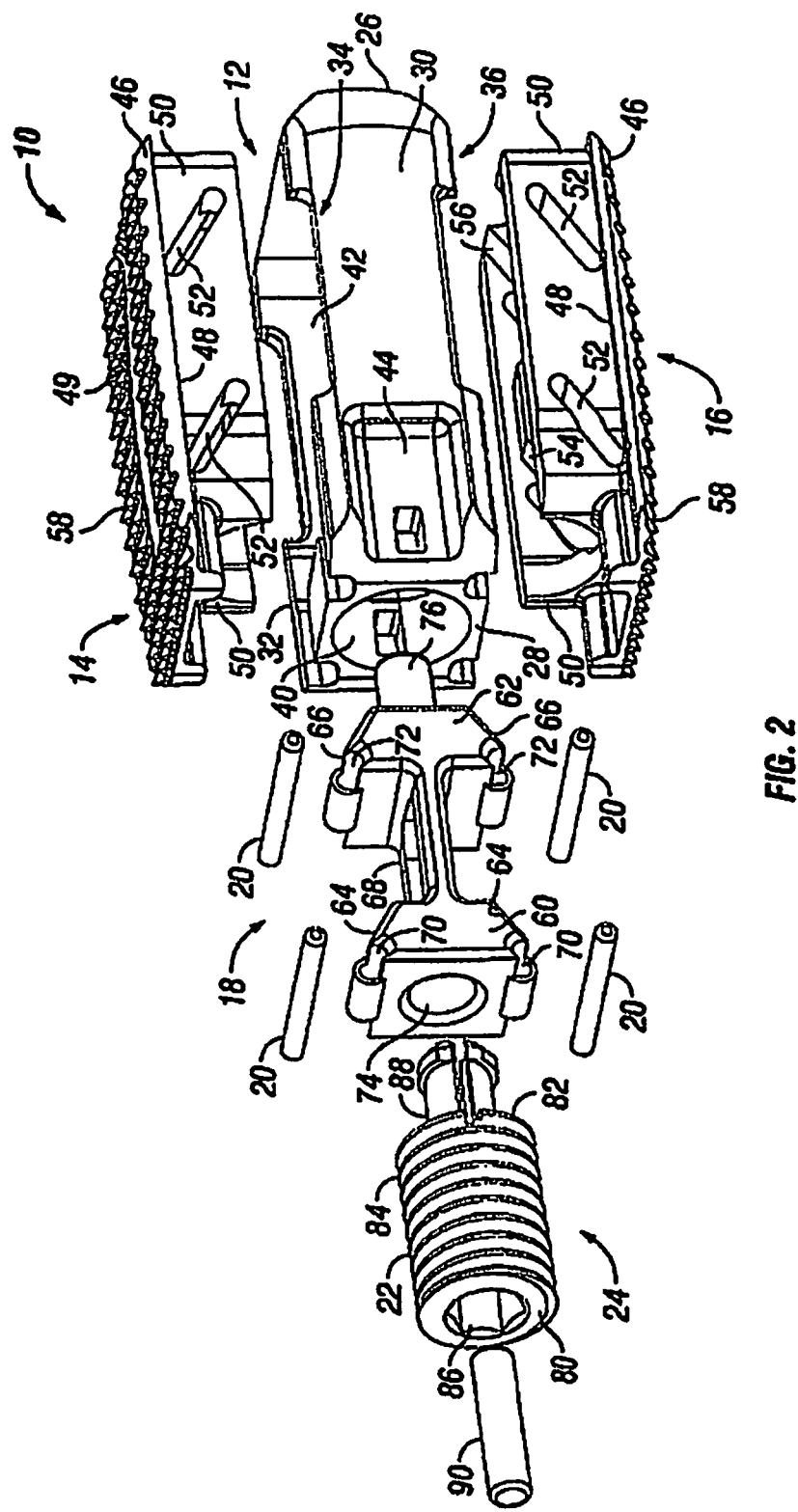
FIG. 2 is an exploded view of the expandable fusion device of FIG. 1.
Figure 3:
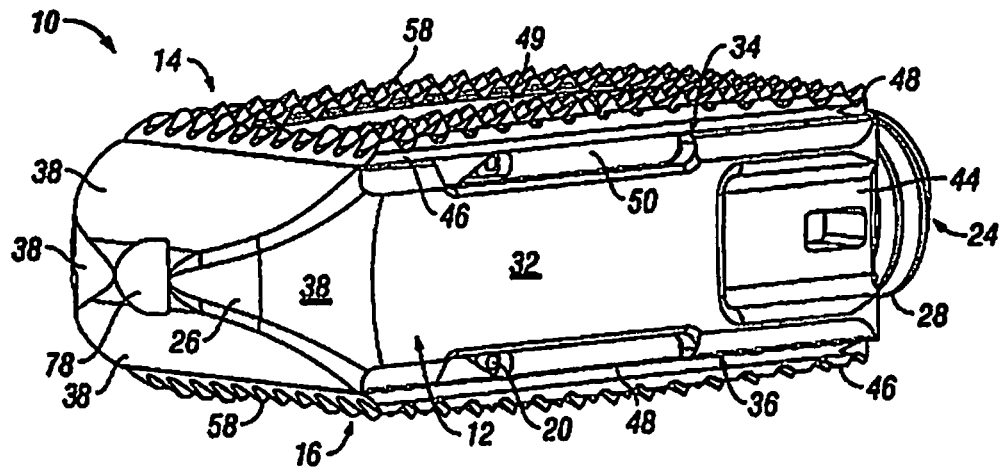
FIG. 3 is a front perspective view of the expandable fusion device of FIG. 1 shown in an unexpanded position

With reference to FIG. 2, an exploded perspective view of one embodiment of the fusion device 10 is shown. In an exemplary embodiment, the fusion device 10 includes a body portion 12, a first endplate 14, a second endplate 16, a translation member 18, a plurality of pins 20, an actuation member 22, and a locking mechanism 24.

With additional reference to FIGS. 3-8, in an exemplary embodiment, the body portion 12 has a first end 26, a second end 28, a first side portion 30 connecting the first end 26 and the second end 28, and a second side portion 32 connecting the first end 26 and the second end 28. The body portion 12 further includes an upper end 34, which is sized to receive at least a portion of the first endplate 14, and a lower end 36, which is sized to receive at least a portion of the second endplate 16.

The first end 26 of the fusion device 10, in an exemplary embodiment, includes at least one angled surface 38, but can include multiple angled surfaces. The angled surface can serve to distract the adjacent vertebral bodies when the fusion device 10 is inserted into an intervertebral space. In another preferred embodiment, it is contemplated that there are at least two opposing angled surfaces forming a generally wedge shaped to distract the adjacent vertebral bodies when the fusion device 10 is inserted into an intervertebral space.

The second end 28 of the body portion 12, in an exemplary embodiment, includes an opening 40 which may include threading. In another exemplary embodiment, the opening 40 may include ratchet teeth instead of threading. The opening 40 extends from the second end 28 of the body portion 12 into a central opening 42 in the body portion 12. In one embodiment, the central opening 42 is sized to receive the translation member 18 and the opening 40 is sized to threadingly receive the actuation member 22. In another exemplary embodiment, the opening 40 is sized to receive the actuation member 22 in a ratcheting fashion. In yet another exemplary embodiment, first side portion 30 and second side portion 32 each include a recess 44 located towards the second end 28 of the body portion 12. The recess 44 is configured and dimensioned to receive an insertion instrument (not shown) that assists in the insertion of the fusion device 10 into an intervertebral space.

Although the following discussion relates to the first endplate 14, it should be understood that it also equally applies to the second endplate 16 as the second endplate 16 is substantially identical to the first endplate 14. Turning now to FIGS. 2-11, in an exemplary embodiment, the first endplate 14 has an upper surface 46, a lower surface 48, and a through opening 49. The through opening 49, in an exemplary embodiment, is sized to receive bone graft or similar bone growth inducing material and further allow the bone graft or similar bone growth inducing material to be packed in the central opening 42 in the body portion 12.

Figure 4:
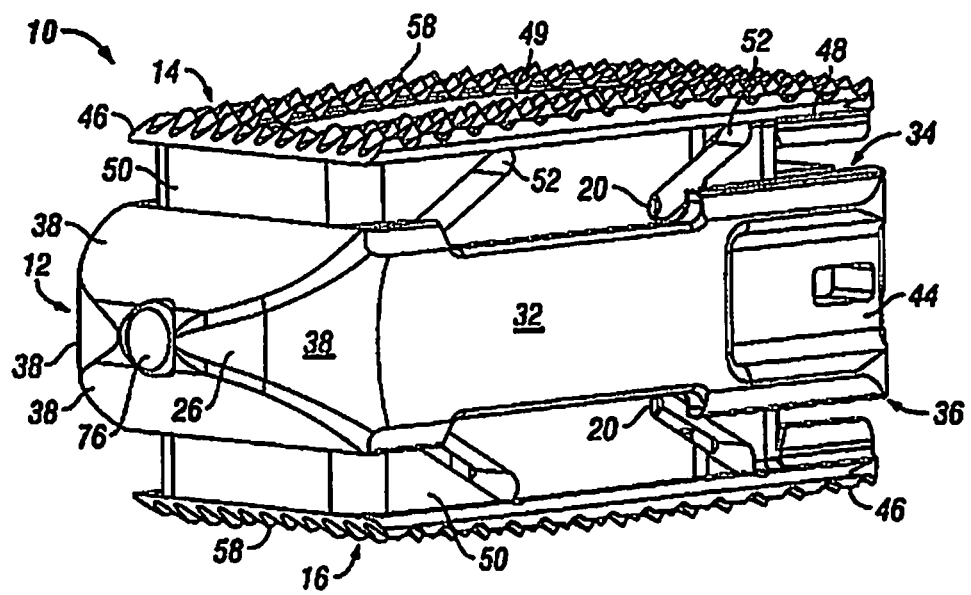
FIG. 4 is a front perspective view of the expandable fusion device of FIG. 1 shown in an expanded position.
Figure 5:
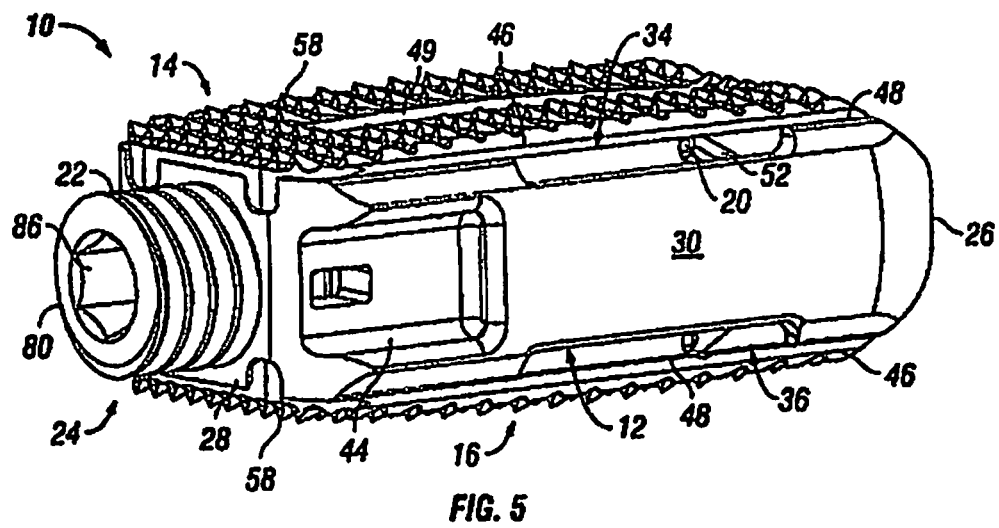
FIG. 5 is a rear perspective view of the expandable fusion device of FIG. 1 shown in an unexpanded position.
Figure 6:
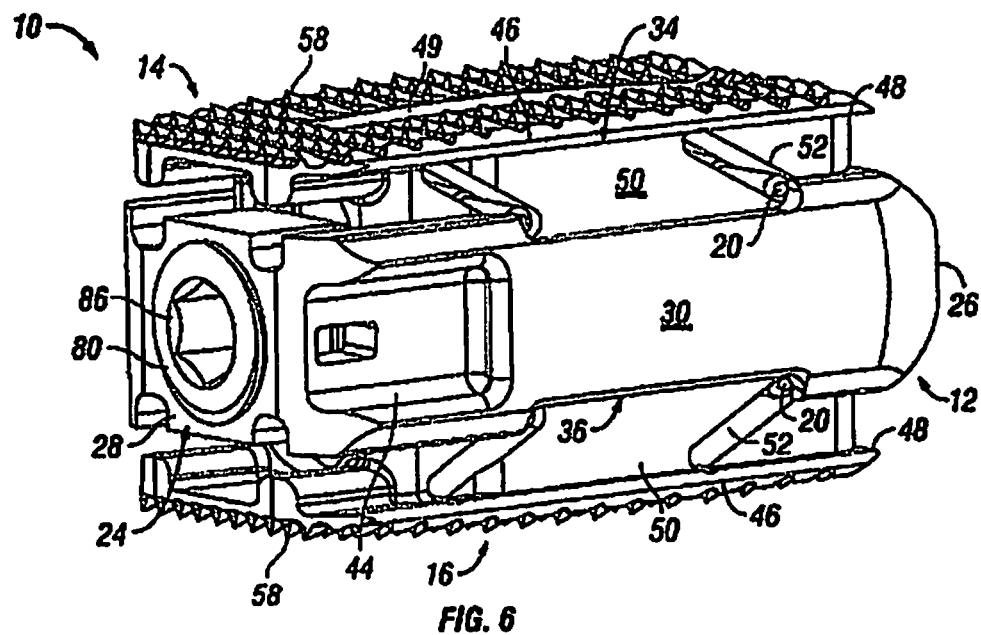
FIG. 6 is a rear perspective view of the expandable fusion device of FIG. 1 shown in an expanded position.
Figure 7:
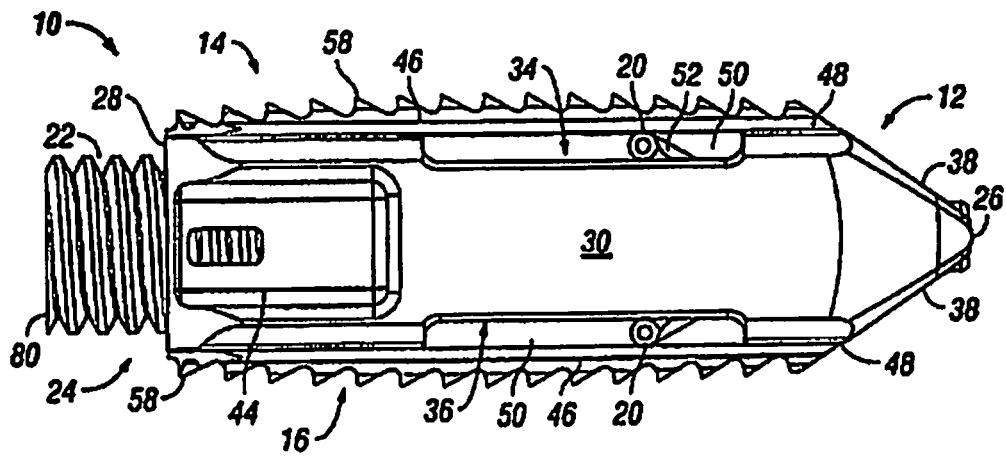
FIG. 7 is a side view of the expandable fusion device of FIG. 1 shown in an unexpanded position.
Figure 8:
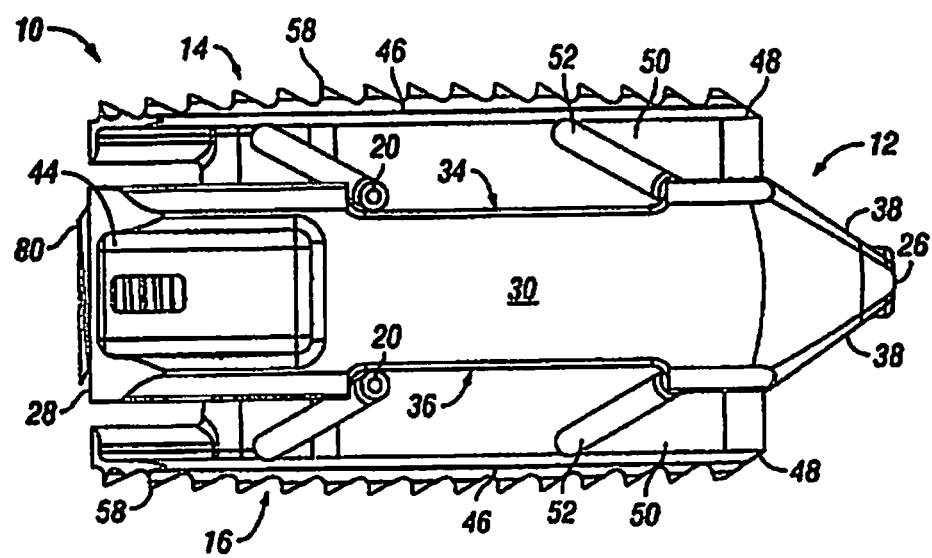
FIG. 8 is a side view of the expandable fusion device of FIG. 1 shown in an expanded position.
Figure 9:
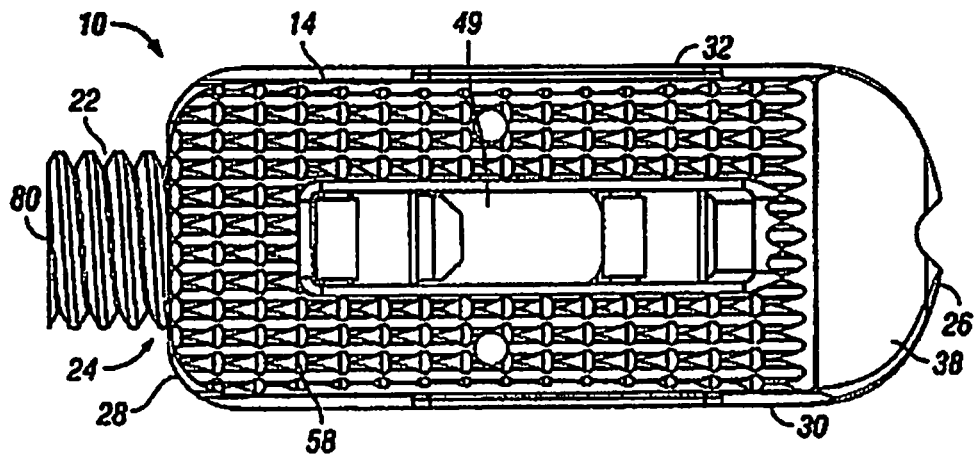
FIG. 9 is a top view of the expandable fusion device of FIG. 1.

In one embodiment, the lower surface 48 includes at least one extension 50 extending along at least a portion of the lower surface 48. As best seen in FIGS. 2 and 4, in an exemplary embodiment, the extension 50 can extend along a substantial portion of the lower surface 48, including, along each side of the endplate 14 and along the front end of the endplate 14. In another exemplary embodiment, the extension 50 includes at least one slot 52, but can include any number of slots 52, including two sets of slots 52 opposing each other, as best seen in FIG. 2. The slots 52 are configured and dimensioned to receive pins 20 and are oriented in an oblique fashion. In another embodiment, the slots 52 may be oriented in a generally vertical orientation.

Figure 12:
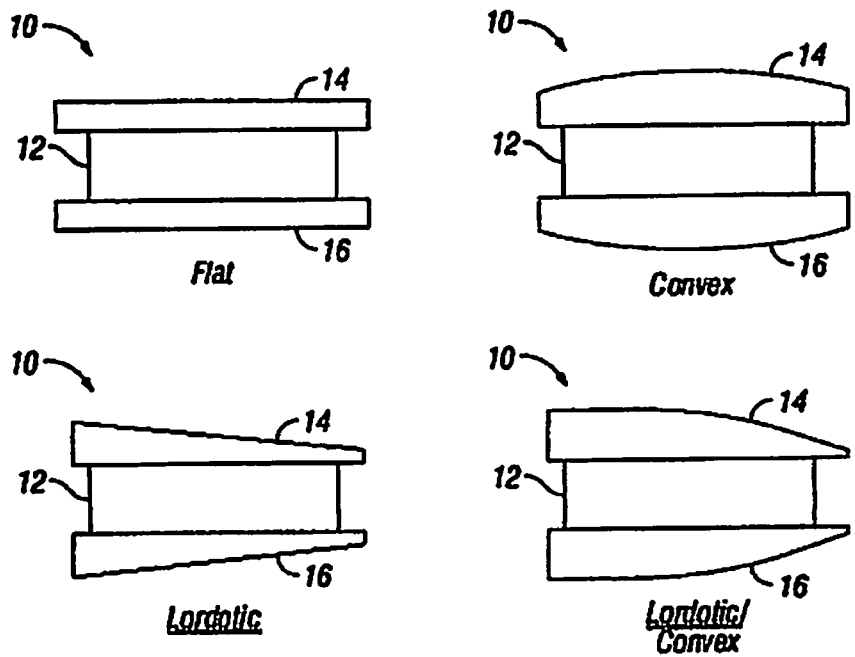
FIG. 12 is a side schematic view of the expandable fusion device of FIG. 1 having different endplates.
Figure 11:
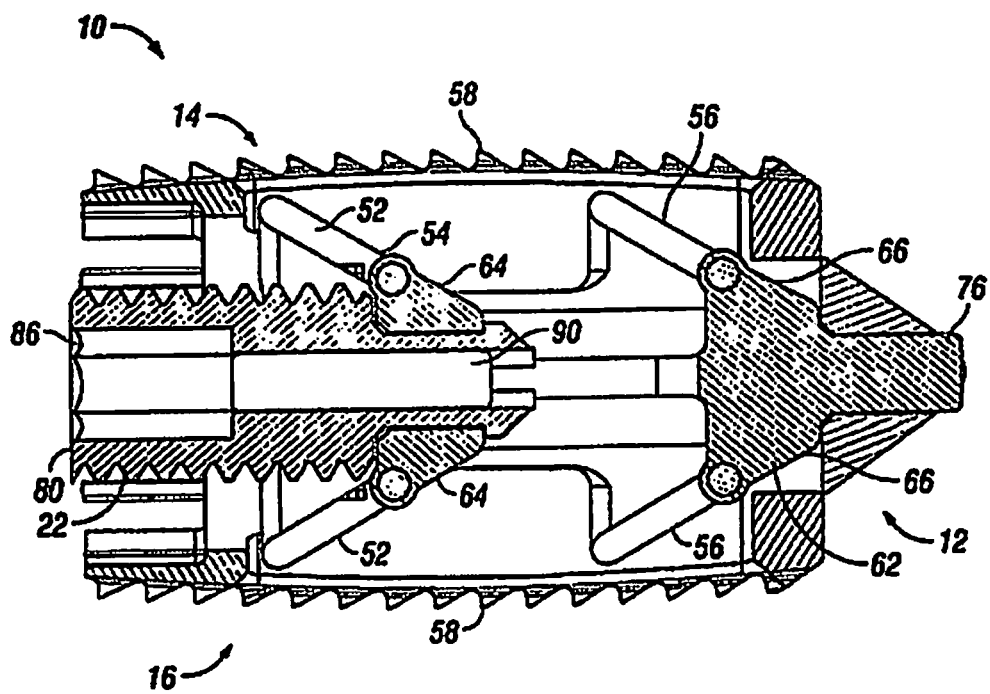
FIG. 11 is a side partial cross-sectional view of the expandable fusion device of FIG. 1 shown in an expanded position.

In an exemplary embodiment, the extension 50 is sized to be received within the central opening 42 of the body portion 12. As best seen in FIGS. 11-12, the lower surface 48 of the first endplate 14 further includes, in an exemplary embodiment, at least one ramped surface 54. In another exemplary embodiment, there are two spaced ramped surfaces 54, 56. It is contemplated that the slope of the ramped surfaces 54, 56 can be equal or can differ from each other. The effect of varying the slopes of the ramped surfaces 54, 56 is discussed below.

Referring now to FIGS. 2-9, in one embodiment, the upper surface 46 of the first endplate 14 is flat and generally planar to allow the upper surface 46 of the endplate 14 to engage with the adjacent vertebral body 2. Alternatively, as shown in FIG. 12, the upper surface 46 can be curved convexly or concavely to allow for a greater or lesser degree of engagement with the adjacent vertebral body 2. It is also contemplated that the upper surface 46 can be generally planar but includes a generally straight ramped surface or a curved ramped surface. The ramped surface allows for engagement with the adjacent vertebral body 2 in a lordotic fashion. Turning back to FIGS. 2-9, in an exemplary embodiment, the upper surface 46 includes texturing 58 to aid in gripping the adjacent vertebral bodies. Although not limited to the following, the texturing can include teeth, ridges, friction increasing elements, keels, or gripping or purchasing projections.

Figure 10:
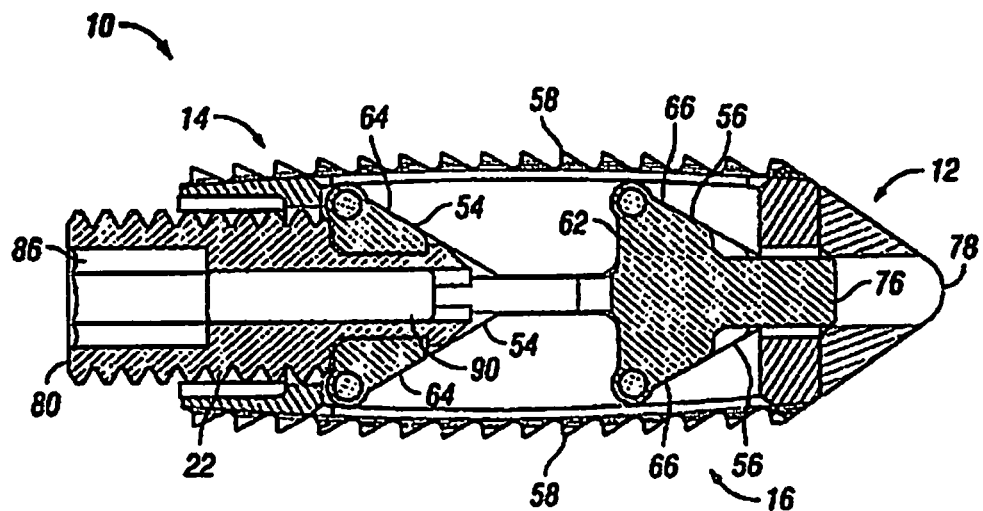
FIG. 10. is a side partial cross-sectional view of the expandable fusion device of FIG. 1 shown in an unexpanded position.

With reference to FIGS. 2 and 10-11, in an exemplary embodiment, the translation member 18 is sized to be received within the central opening 42 of the body portion 12 and includes at least a first expansion portion 60. In another embodiment, the translation member 18 includes a first expansion portion 60 and a second expansion portion 62, the expansion portions 60, 62 being connected together via a bridge portion 68. It is also contemplated that there may be more than two expansion portions where each of the expansion portions is connected by a bridge portion. The expansion portions 60, 62 each have angled surfaces 64, 66 configured and dimensioned to engage the ramp surfaces 54, 56 of the first and second endplates 14, 16. In an exemplary embodiment, the translation member 18 also includes recesses 70, 72, the recesses 70, 72 are sized to receive and retain pins 20. In one embodiment, the expansion portion 60 includes an opening 74, which is sized to receive a portion of the actuation member 22, and the expansion portion 62 includes a nose 76, which is received within an opening 78 in the first end 26 to stabilize the translation member 18 in the central opening 42 of the body member 12.

In an exemplary embodiment, the actuation member 22 has a first end 80, a second end 82 and threading 84 extending along at least a portion thereof from the first end 80 to the second end 82. The threading 84 threadingly engages the threading extending along a portion of opening 40 in the body portion 12. In another exemplary embodiment, the actuation member 22 includes ratchet teeth instead of threading. The ratchet teeth engage corresponding ratchet teeth in the opening 40 in the body portion 12. The first end 80 includes a recess 86 dimensioned to receive an instrument (not shown) that is capable of advancing the actuation member 22 with respect to the body portion 12 of the fusion device 10. The second end 82 of the actuation member 22 includes an extension 88 that is received within the opening 74 of the expansion portion 60. In one embodiment, the extension 88 may include a plurality of slits and a lip portion. The plurality of slits allows the extension portion 88 to flex inwardly reducing its diameter when received in the opening 74. Once the lip portion of the extension portion 88 is advanced beyond the end of the opening 74, the extension portion 88 will return back to its original diameter and the lip portion will engage the expansion portion 60. It is further contemplated that a pin member 90 can be included to prevent the extension portion from flexing inwardly thereby preventing the actuation member 22 from disengaging from the translation member 18.

In an exemplary embodiment, the fusion device 10 can further include a locking mechanism 24. The mechanism 24 is designed to resist rotation of the actuation member 22 rather than prevent rotation of the actuation member 22. In an exemplary embodiment, either deformable threading can be included on actuation member 22 or a disruption of the threading may be included where a deformable material is included in the threading disruption. It is contemplated that the deformable member or deformable threading can be made from a deformable or elastic, biocompatible material such as nitinol or PEEK.

Turning now to FIGS. 1-8 and 10-11, a method of installing the expandable fusion device 10 is now discussed. Prior to insertion of the fusion device 10, the intervertebral space is prepared. In one method of installation, a diskectomy is performed where the intervertebral disc, in its entirety, is removed. Alternatively, only a portion of the intervertebral disc can be removed. The endplates of the adjacent vertebral bodies 2, 3 are then scraped to create an exposed end surface for facilitating bone growth across the invertebral space. The expandable fusion device 10 is then introduced into the intervertebral space, with the first end 26 being inserted first into the disc space followed by the second end 28. In an exemplary method, the fusion device 10 is in the unexpanded position when introduced into the intervertebral space. The wedged shaped first end 26 will assist in distracting the adjacent vertebral bodies 2, 3 if necessary. This allows for the option of having little to no distraction of the intervertebral space prior to the insertion of the fusion device 10. In another exemplary method, the intervertebral space may be distracted prior to insertion of the fusion device 10. The distraction provide some benefits by providing greater access to the surgical site making removal of the intervertebral disc easier and making scraping of the endplates of the vertebral bodies 2, 3 easier.

With the fusion device 10 inserted into and seated in the appropriate position in the intervertebral disc space, the fusion device can then expanded into the expanded position, as best seen in FIGS. 1, 4, 6, 8, and 11. To expand the fusion device 10, an instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a first direction, the actuation member 22 and the translation member 18 move with respect to the body portion 12 toward the first end 26 of the body portion 12. In another exemplary embodiment, the actuation member 22 is moved in a linear direction with the ratchet teeth engaging as means for controlling the movement of the actuation member 22 and the translation member 18. As the translation member 18 moves, the ramped surface 64, 66 of the expansion portions 60, 62 push against the ramped surfaces 54, 56 of the endplates 14, 16 pushing endplates 14, 16 outwardly into the expanded position. This can best be seen in FIGS. 10 and 11. Since the expansion of the fusion device 10 is actuated by a rotational input, the expansion of the fusion device 10 is infinite. In other words, the endplates 14, 16 can be expanded to an infinite number of heights dependent on the rotational advancement of the actuation member 22. As discussed above, the fusion device 10 includes a locking mechanism 24 which assists in retaining the endplates 14, 16 at the desired height.

Figure 13:
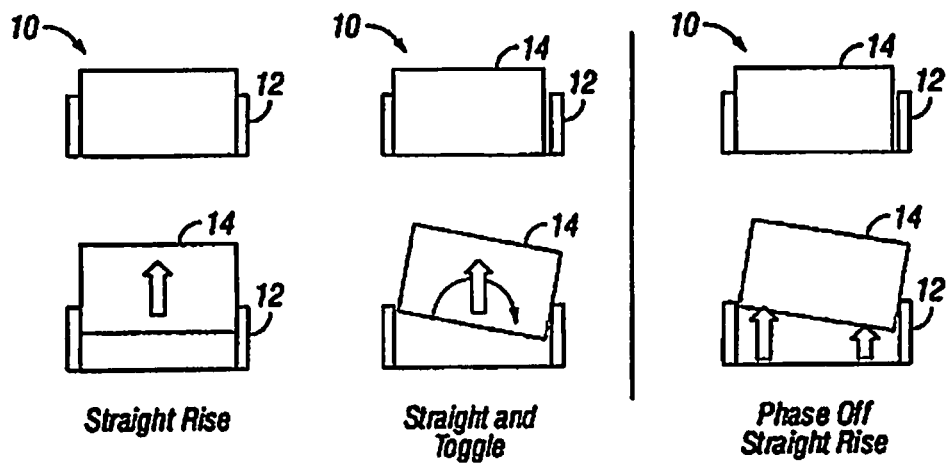
FIG. 13 is a partial side schematic view of the expandable fusion device of FIG. 1 showing different modes of endplate expansion.

It should also be noted that the expansion of the endplates 14, 16 can be varied based on the differences in the dimensions of the ramped surfaces 54, 56, 64, 66. As best seen in FIG. 13, the endplates 14, 16 can be expanded in any of the following ways: straight rise expansion, straight rise expansion followed by a toggle into a lordotic expanded configuration, or a phase off straight rise into a lordotic expanded configuration.

Turning back to FIGS. 1-8 and 10-11, in the event the fusion device 10 needs to be repositioned or revised after being installed and expanded, the fusion device 10 can be contracted back to the unexpanded configuration, repositioned, and expanded again once the desired positioning is achieved. To contract the fusion device 10, the instrument is engaged with recess 86 in the actuation member 22. The instrument is used to rotate actuation member 22. As discussed above, actuation member 22 is threadingly engaged body portion 12 and is engaged with translation member 18; thus, as the actuation member 22 is rotated in a second direction, opposite the first direction, the actuation member 22 and translation member 18 move with respect to the body portion 12 toward the second end 28 of the body portion 12. As the translation member 18 moves, the pins 20, a portion of which are located within the slots 52, ride along the slots 52 pulling the endplates 14, 16 inwardly into the unexpanded position.

Figure 14:
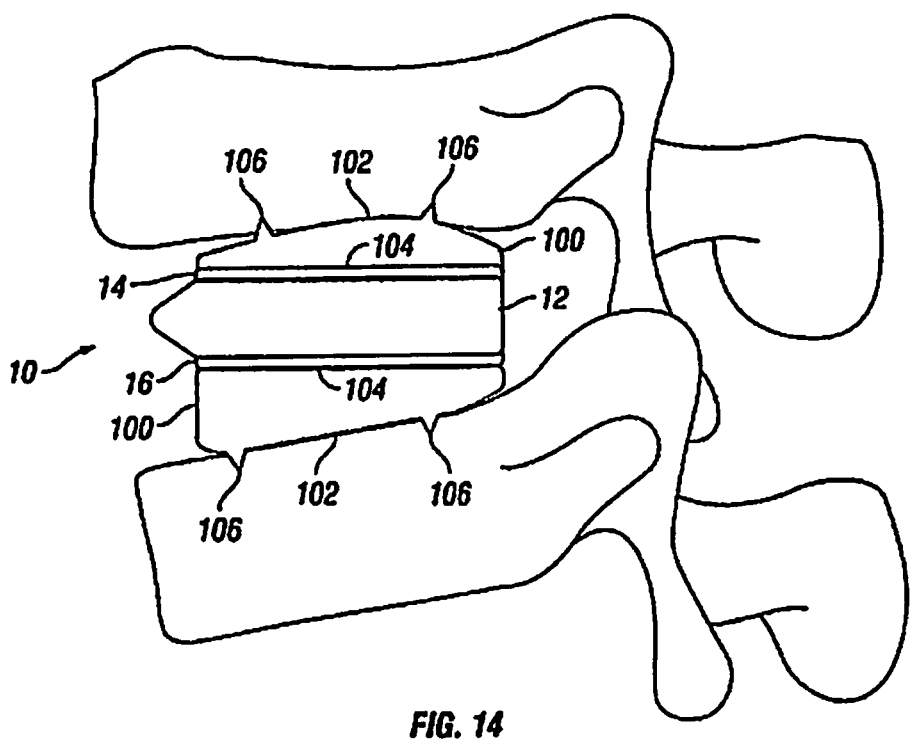
FIG. 14 is a side schematic view of the expandable fusion device of FIG. 1 with artificial endplates shown between adjacent vertebrae.

With reference now to FIG. 14, fusion device 10 is shown with an exemplary embodiment of artificial endplates 100. Artificial endplates 100 allows the introduction of lordosis even when the endplates 14 and 16 of the fusion device 10 are generally planar. In one embodiment, the artificial endplates 100 have an upper surface 102 and a lower surface 104. The upper surfaces 102 of the artificial endplates 100 have at least one spike 106 to engage the adjacent vertebral bodies. The lower surfaces 104 have complementary texturing or engagement features on their surfaces to engage with the texturing or engagement features on the upper endplate 14 and the lower endplate 16 of the fusion device 10. In an exemplary embodiment, the upper surface 102 of the artificial endplates 100 have a generally convex profile and the lower surfaces 104 have a generally parallel profile to achieve lordosis. In another exemplary embodiment, fusion device 10 can be used with only one artificial endplate 100 to introduce lordosis even when the endplates 14 and 16 of the fusion device 10 are generally planar. The artificial endplate 100 can either engage endplate 14 or engage endplate 16 and function in the same manner as described above with respect to two artificial endplates 100.

Although the preceding discussion only discussed having a single fusion device 10 in the intervertebral space, it is contemplated that more than one fusion device 10 can be inserted in the intervertebral space. It is further contemplated that each fusion device 10 does not have to be finally installed in the fully expanded state. Rather, depending on the location of the fusion device 10 in the intervertebral disc space, the height of the fusion device 10 may vary from unexpanded to fully expanded.

Figure 16:
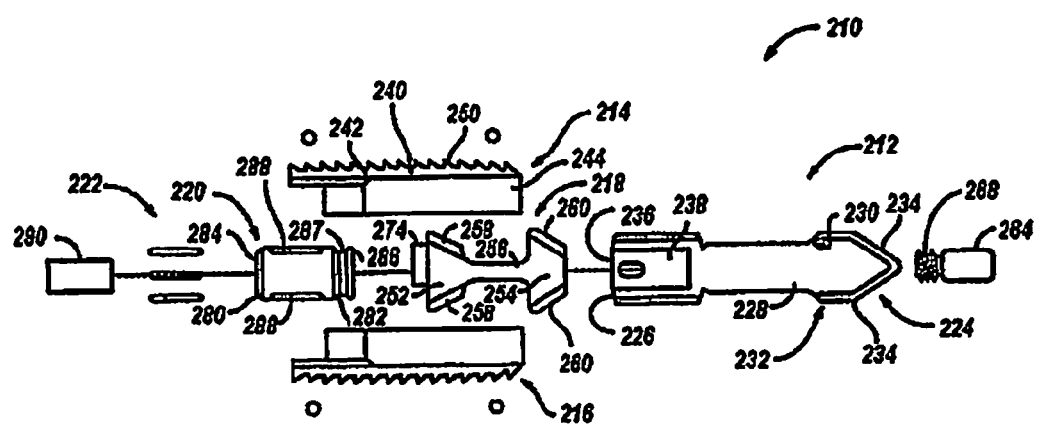
FIG. 16 is an exploded view of the expandable fusion device of FIG. 15.

With reference to FIG. 16, an exploded perspective view of one embodiment of the fusion device 210 is shown. In an exemplary embodiment, the fusion device 210 includes a body portion 212, a first endplate 214, a second endplate 216, a translation member 218, an actuation member 220, and an insert 222.

With additional reference to FIGS. 17-20, in an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The body portion 212 further includes an upper end 230, which is sized to receive at least a portion of the first endplate 214, and a lower end 232, which is sized to receive at least a portion of the second endplate 216.

The first end 224 of the body portion 212, in an exemplary embodiment, includes at least one angled surface 234, but can include multiple angled surfaces. The angled surface 234 can serve to distract the adjacent vertebral bodies when the fusion device 210 is inserted into an intervertebral space. In another preferred embodiment, it is contemplated that there are at least two opposing angled surfaces forming a generally wedge shaped to distract the adjacent vertebral bodies when the fusion device 210 is inserted into an intervertebral space.

The second end 226 of the body portion 212, in an exemplary embodiment, includes an opening 236 which may include threading. In another exemplary embodiment, the opening 236 may include ratchet teeth instead of threading. The opening 236 extends from the second end 226 of the body portion 212 into a central opening (not illustrated) in the body portion 212. In one embodiment, the central opening is sized to receive the translation member 218, and the opening 236 is sized to threadingly receive the actuation member 220. In another exemplary embodiment, the opening 236 is sized to receive the actuation member 220 in a ratcheting fashion. In yet another exemplary embodiment, first side portion 228 and second side portion 229 each include a recess 238 located towards the second end 226 of the body portion 212. The recess 238 is configured and dimensioned to receive an insertion instrument (not shown) that assists in the insertion of the fusion device 210 into an intervertebral space.

Although the following discussion relates to the first endplate 214, it should be understood that it also equally applies to the second endplate 216 as the second endplate 216 is substantially identical to the first endplate 214 in embodiments of the present invention. Turning now to FIGS. 16-20, in an exemplary embodiment, the first endplate 214 has an upper surface 240, a lower surface 242, and a through opening 243. The through opening 243, in an exemplary embodiment, is sized to receive bone graft or similar bone growth inducing material and further allow the bone graft or similar bone growth inducing material to be packed in the central opening in the body portion 212.

Figure 17:
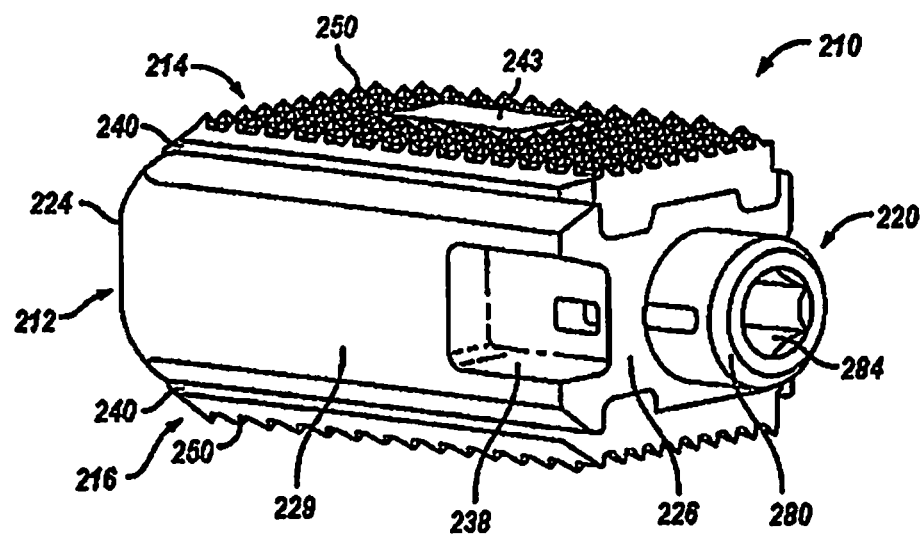
FIG. 17 is a rear perspective view of the expandable fusion device of FIG. 15 shown in an unexpanded position.
Figure 18:
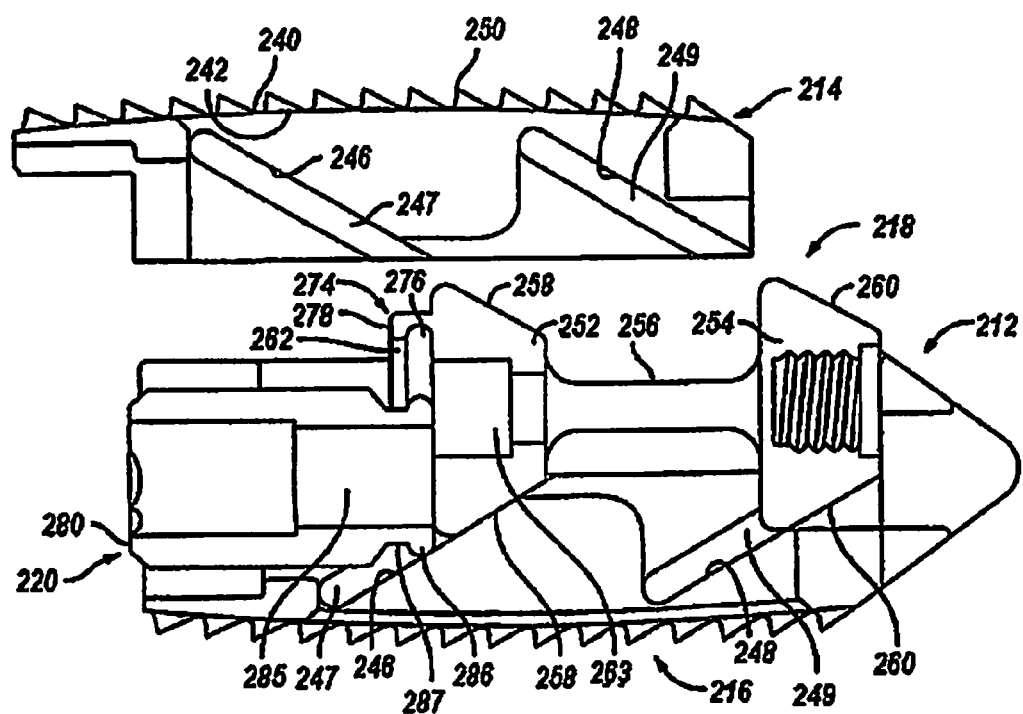
FIG. 18 is a side cross-sectional view of the expandable fusion device of FIG. 15 shown with one of the endplates removed.

In one embodiment, the lower surface 242 includes at least one extension 244 extending along at least a portion of the lower surface 242. As best seen in FIGS. 17 and 18, in an exemplary embodiment, the extension 244 can extend along a substantial portion of the lower surface 242, including, along each side of the endplate 214 and along the front end of the endplate 214. In another exemplary embodiment, the extension 244 includes at least one ramped portion 246, but can include any number of ramped portions, including two spaced ramped portions 246, 248 in the extension 244 that extend between each side of the endplate 214, as best seen in FIG. 18. It is contemplated that the slope of the ramped portions 246, 248 can be equal or can differ from each other. The effect of varying the slopes of the ramped portions 246, 248 is discussed below.

In an exemplary embodiment, the ramped portions 246, 248 further include grooved portions 247, 249 that are configured and dimensioned to receive angled surfaces 258, 260 of the translation member 218 and are oriented in an oblique fashion. In a preferred embodiment, the grooved portions 246, 248 are dovetail grooves configured and dimensioned to hold the angled surfaces 258, 260 of the translation member 218 while allowing the angles surfaces 258, 260 to slide against the ramped portions 246, 248.

Referring now to FIGS. 17-20, in one embodiment, the upper surface 240 of the first endplate 214 is flat and generally planar to allow the upper surface 240 of the endplate 214 to engage with the adjacent vertebral body 202. Alternatively, as shown in FIG. 21, the upper surface 240 can be curved convexly or concavely to allow for a greater or lesser degree of engagement with the adjacent vertebral body 202. It is also contemplated that the upper surface 240 can be generally planar but includes a generally straight ramped surface or a curved ramped surface. The ramped surface allows for engagement with the adjacent vertebral body 202 in a lordotic fashion. Turning back to FIGS. 16-20, in an exemplary embodiment, the upper surface 240 includes texturing 250 to aid in gripping the adjacent vertebral bodies. Although not limited to the following, the texturing can include teeth, ridges, friction increasing elements, keels, or gripping or purchasing projections.

Figure 19:
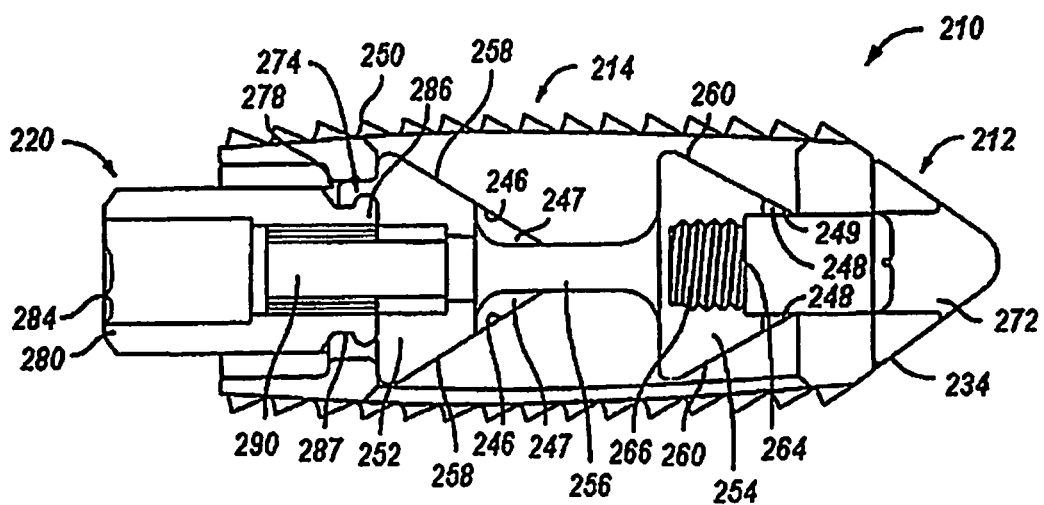
FIG. 19 is a side partial cross-sectional view of the expandable fusion device of FIG. 15 shown in an unexpanded position.
Figure 20:
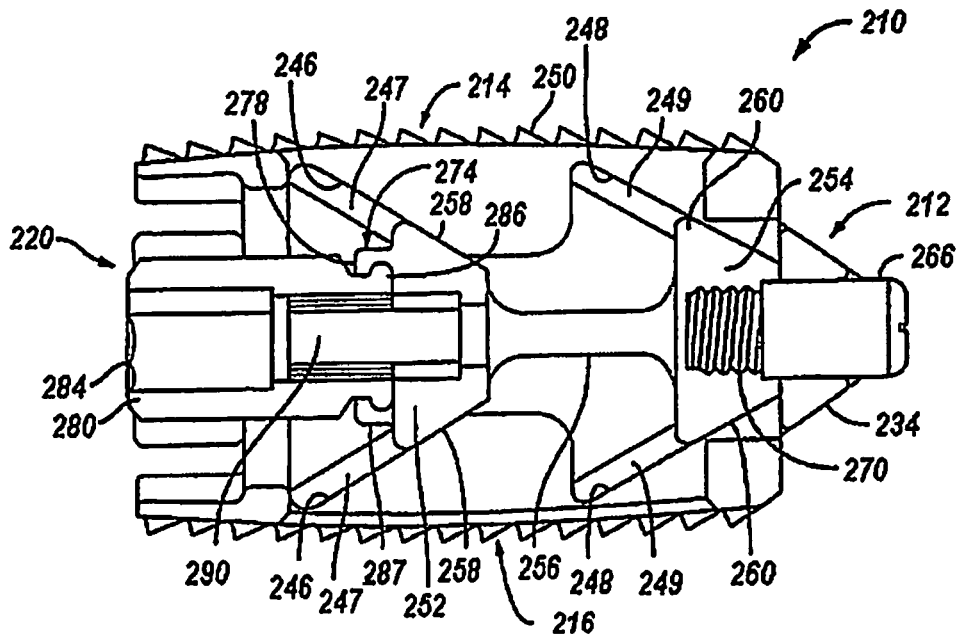
FIG. 20 is a side partial cross-sectional view of the expandable fusion device of FIG. 15 shown in an expanded position.
Figure 21:
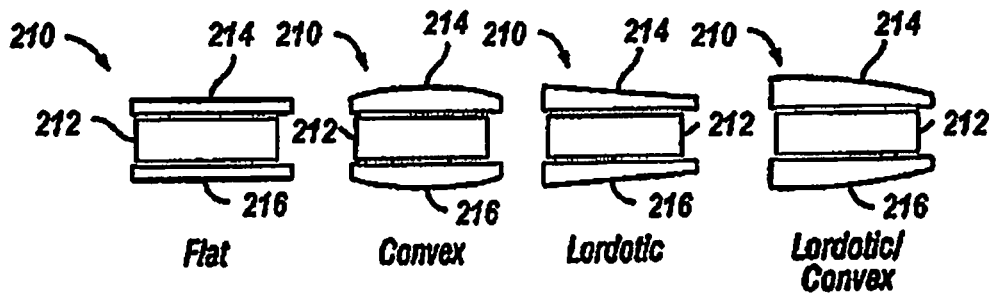
FIG. 21 is a side schematic view of the expandable fusion device of FIG. 15 having different endplates.

With reference to FIGS. 16 and 18-20, in an exemplary embodiment, the translation member 218 is sized to be received within the central opening of the body portion 212 and includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260 configured and dimensioned to engage the grooved portions 246, 248 of the first and second endplates 214, 216. In one embodiment, the translation member 218 includes an opening 262 in the first expansion portion 252, which is sized to receive a portion of the actuation member 220, as best seen in FIG. 18. In an exemplary embodiment, the first expansion portion 252 includes a central bore 263 that extends from the opening 262 and through the first expansion portion 252. In one embodiment, the translation member 218 includes a hole 264 in the second expansion portion 254, which is sized to receive nose 266, as best seen in FIGS. 19 and 20. In an exemplary embodiment, the hole 264 includes threading 268 for threadedly receiving a threaded end 270 of the nose 266, as shown on FIG. 20. The nose 266 is received in an opening 272 in the first end 234 of the body portion 212 to stabilize the translation member 218 in the central opening of the body portion 212.

In one embodiment, the translation member 218 includes a locking mechanism 274, which is configured and adapted to engage the actuation member 220. As illustrated, the locking mechanism 274 may extend from the first expansion portion 252. The locking mechanism 274 includes a slot 276 configured and adapted to receive extension 287 of the actuation member 220. In an exemplary embodiment, the locking mechanism 274 further includes a stop 278 (e.g., a rim, a lip, etc.) that engages the actuation member 220 when it is disposed in the slot 276.

Referring now to FIGS. 16-20, in an exemplary embodiment, the actuation member 220 has a first end 280, a second end 282, and threading (not illustrated) extending along at least a portion thereof from the first end 280 to the second end 282. The threading threadingly engages the threading that extends along a portion of opening 236 in the body portion 212. In another exemplary embodiment, the actuation member 220 includes ratchet teeth instead of threading. The ratchet teeth engage corresponding ratchet teeth in the opening 236 in the body portion 212. The first end 280 includes a recess 284 dimensioned to receive an instrument (not shown) that is capable of advancing the actuation member 220 with respect to the body portion 212 of the fusion device 210. In an embodiment, the actuation member 220 includes a bore 285, as best seen by FIG. 18, that extends from the recess 284 in the first end to the second 282. The second end 282 of the actuation member 220 includes an extension 286 that is received within the opening 262 in the first expansion portion 252. In one embodiment, the extension 288 may include a lip portion 286 and a plurality of slits 288. The plurality of slits 288 are configured to receive inserts 222. Inserts 222 are provided to limit motion of the actuation member 220. Once the lip portion 286 is placed into the slot 276 of the locking mechanism 274, the lip portion 286 will engage the stop 278 preventing longitudinal movement of the actuation member 220 with respect to the translation member 218. It is further contemplated that a pin member 290 can be included to further secure the actuation member 220 in the translation member 219. In an embodiment, the pin member 290 can be pressed into the central bore 285 of the actuation member 220 and the central bore 263 of the translation member, thereby preventing the actuation member 220 from disengaging from the translation member 218. Additionally, in an exemplary embodiment, the fusion device 210 can further include a chamfered tip 224 for distraction of adjacent vertebrae.

Turning now to FIGS. 15-20, a method of installing the expandable fusion device 210 is now discussed. Prior to insertion of the fusion device 210, the intervertebral space is prepared. In one method of installation, a discectomy is performed where the intervertebral disc, in its entirety, is removed. Alternatively, only a portion of the intervertebral disc can be removed. The endplates of the adjacent vertebral bodies 202, 203 are then scraped to create an exposed end surface for facilitating bone growth across the invertebral space. The expandable fusion device 210 is then introduced into the intervertebral space, with the first end 222 of the body portion 212 being inserted first into the disc space followed by the second end 224. In an exemplary method, the fusion device 210 is in the unexpanded position when introduced into the intervertebral space. The wedged-shaped first end 222 should assist in distracting the adjacent vertebral bodies 202, 203, if necessary. This allows for the option of having little to no distraction of the intervertebral space prior to the insertion of the fusion device 210. In another exemplary method, the intervertebral space may be distracted prior to insertion of the fusion device 210. The distraction provide some benefits by providing greater access to the surgical site making removal of the intervertebral disc easier and making scraping of the endplates of the vertebral bodies 202, 203 easier.

Figure 15:
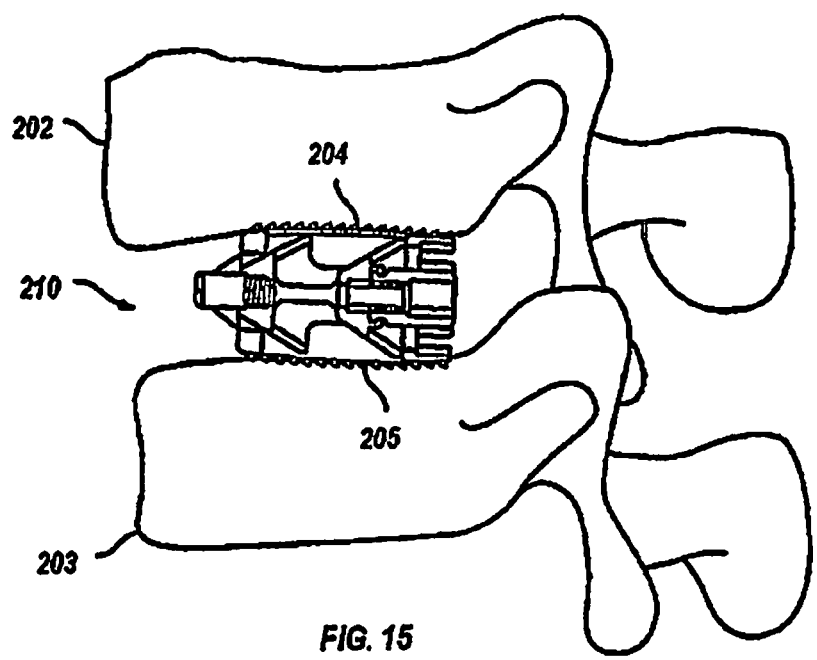
FIG. 15 is a side view of an embodiment of an expandable fusion device shown between adjacent vertebrae according to the present invention.

With the fusion device 210 inserted into and seated in the appropriate position in the intervertebral disc space, the fusion device can then expanded into the expanded position, as best seen in FIGS. 15, 19, and 20. To expand the fusion device 210, an instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a first direction, the actuation member 220 and the translation member 218 move with respect to the body portion 212 toward the first end 222 of the body portion 212. In another exemplary embodiment, the actuation member 220 is moved in a linear direction with the ratchet teeth engaging as means for controlling the movement of the actuation member 220 and the translation member 218. As the translation member 218 moves, the angled surfaces 258, 260 of the expansion portions 252, 254 push against the ramped portions 246, 248 of the endplates 214, 216 pushing endplates 214, 216 outwardly into the expanded position with the angled surfaces 258, 260 riding along the grooved portions 247, 248 of the ramped portions 246, 248. This can best be seen in FIGS. 19 and 20. Since the expansion of the fusion device 210 is actuated by a rotational input, the expansion of the fusion device 210 is infinite. In other words, the endplates 214, 216 can be expanded to an infinite number of heights dependent on the rotational advancement of the actuation member 220. As discussed above, the fusion device 210 includes a locking mechanism 222 which assists in retaining the endplates 14, 16 at the desired height.

Figure 22:
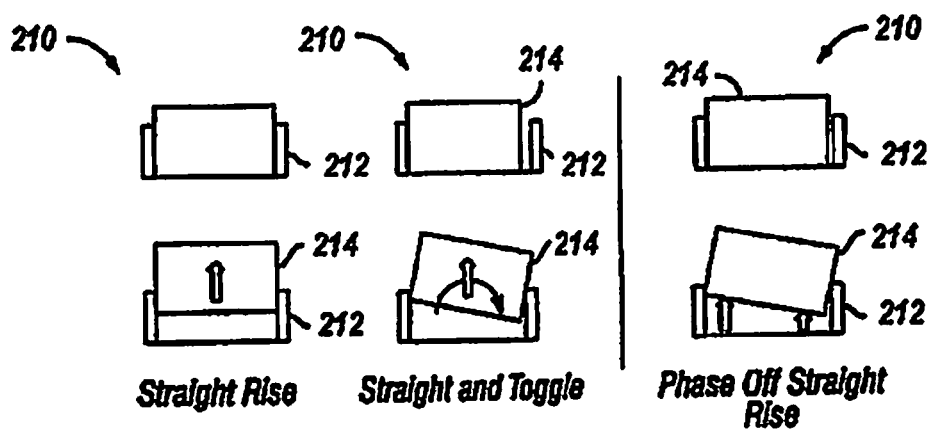
FIG. 22 is a partial side schematic view of the expandable fusion device of FIG. 15 showing different modes of endplate expansion.

It should also be noted that the expansion of the endplates 214, 216 can be varied based on the differences in the dimensions of the ramped portions 246, 248 and the angled surfaces 258, 260. As best seen in FIG. 22, the endplates 214, 216 can be expanded in any of the following ways: straight rise expansion, straight rise expansion followed by a toggle into a lordotic expanded configuration, or a phase off straight rise into a lordotic expanded configuration.

Turning back to FIGS. 15-20, in the event the fusion device 210 needs to be repositioned or revised after being installed and expanded, the fusion device 210 can be contracted back to the unexpanded configuration, repositioned, and expanded again once the desired positioning is achieved. To contract the fusion device 210, the instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a second direction, opposite the first direction, the actuation member 220 and translation member 218 move with respect to the body portion 212 toward the second end 226 of the body portion 212. As the translation member 218 moves, the angled surfaces 258, 260 of the translation member 218 ride along the grooved portions 247, 249 pulling the endplates 214, 216 inwardly into the unexpanded position.

Figure 23:
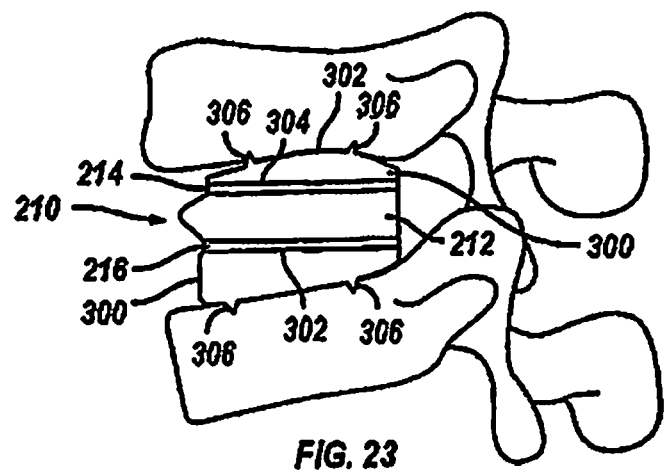
FIG. 23 is a side schematic view of the expandable fusion device of FIG. 15 with artificial endplates shown between adjacent vertebrae.

With reference now to FIG. 23, fusion device 210 is shown with an exemplary embodiment of artificial endplates 300. Artificial endplates 300 allows the introduction of lordosis even when the endplates 214 and 216 of the fusion device 210 are generally planar. In one embodiment, the artificial endplates 300 have an upper surface 302 and a lower surface 304. The upper surfaces 302 of the artificial endplates 300 have at least one spike 306 to engage the adjacent vertebral bodies. The lower surfaces 304 have complementary texturing or engagement features on their surfaces to engage with the texturing or engagement features on the upper endplate 214 and the lower endplate 216 of the fusion device 210. In an exemplary embodiment, the upper surface 302 of the artificial endplates 300 have a generally convex profile and the lower surfaces 304 have a generally parallel profile to achieve lordosis. In another exemplary embodiment, fusion device 210 can be used with only one artificial endplate 300 to introduce lordosis even when the endplates 214 and 216 of the fusion device 210 are generally planar. The artificial endplate 300 can either engage endplate 214 or engage endplate 216 and function in the same manner as described above with respect to two artificial endplates 300.

Figure 24:
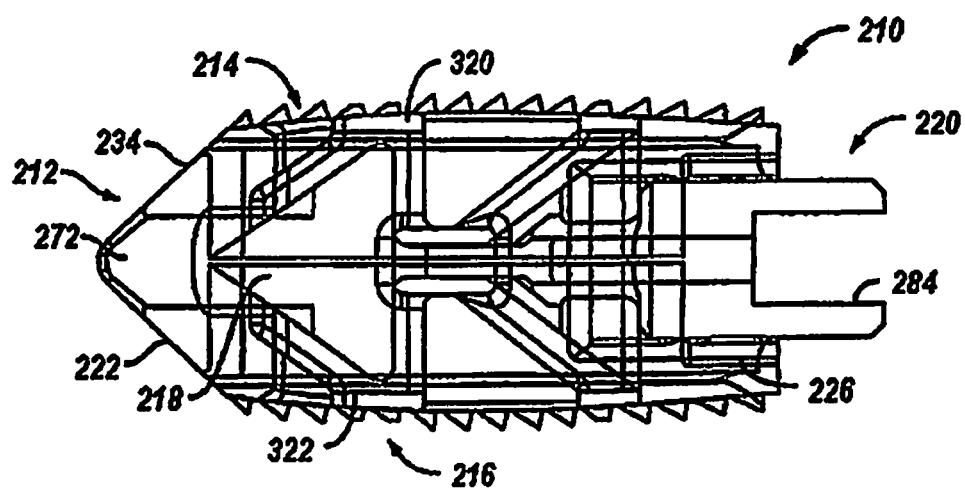
FIG. 24 is a side view cross-sectional view of another embodiment of an expandable fusion device shown in an unexpanded position.
Figure 25:
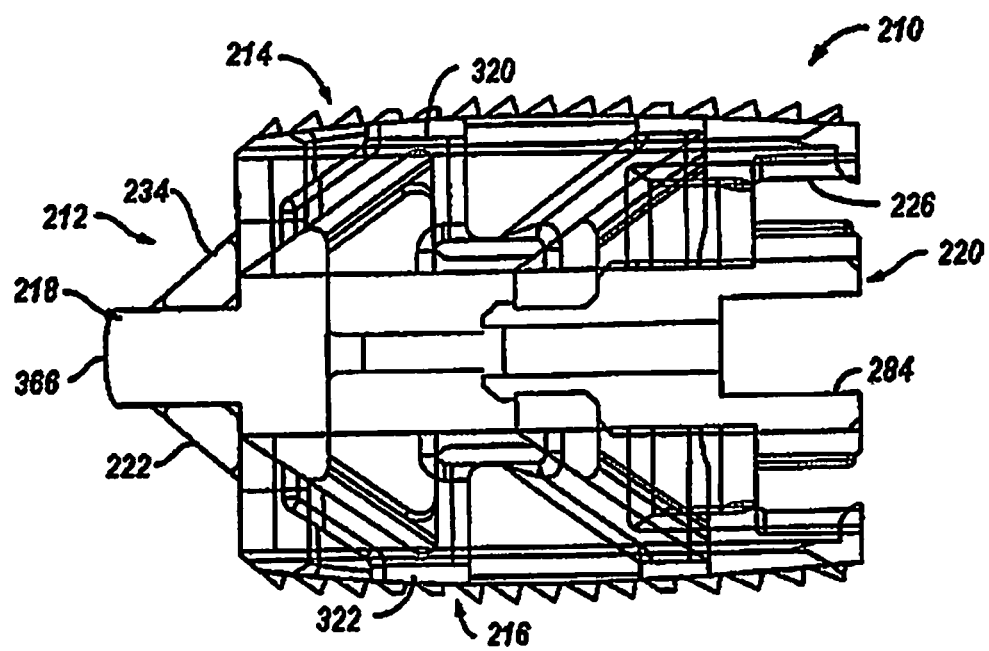
FIG. 25 is a side view cross-sectional view of the expandable fusion device of FIG. 24 shown in an expanded position.
Figure 26:
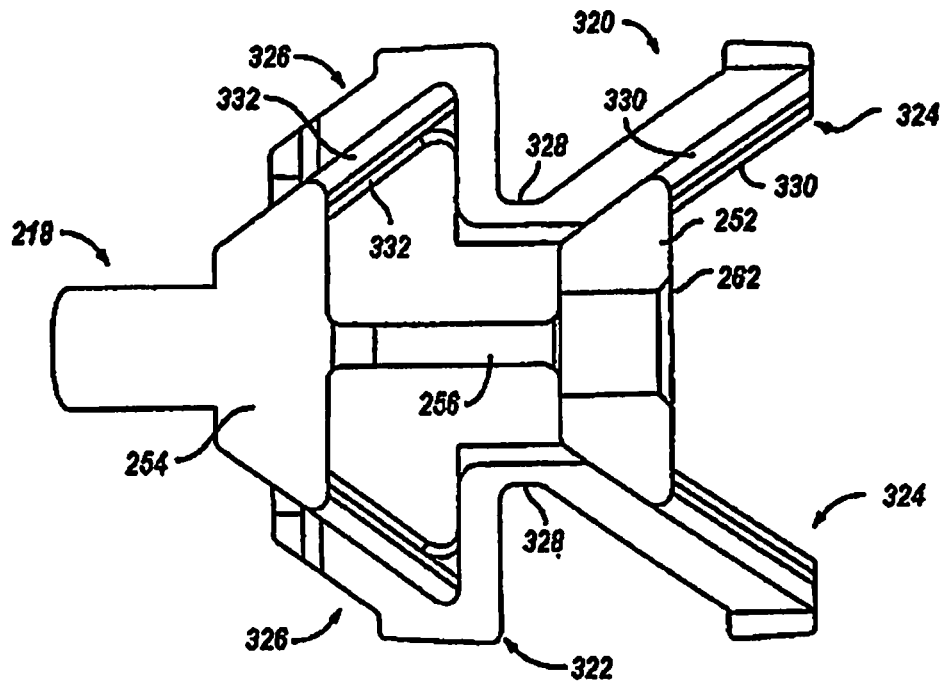
FIG. 26 is a side view of the expandable fusion device of FIG. 24 showing the translation member and the ramped insert.

Referring now to FIGS. 24 and 25, an alternative embodiment of the fusion device 210 is shown. In an exemplary embodiment, the fusion device 210 includes a body portion 212, a first endplate 214, a second endplate 216, a translation member 218, and an actuation member 220. In the illustrated embodiment, the fusion device further includes a first ramped insert 320 and a second ramped insert 322.

Although the following discussion relates to the first ramped insert 320, it should be understood that it also equally applies to the second ramped insert 322 as the second ramped insert 322 is substantially identical to the first ramped insert 320 in embodiments of the present invention. Turning now to FIGS. 24-27, in an exemplary embodiment, the first ramped insert 320 includes a first ramped portion 324 and a second ramped portion 326, the first and second ramped portions 324, 326 being connected by a bridge portion 328. The ramped portions 324, 326 each have grooved portions 330, 332 configured and dimensioned to receive angled surfaces 258, 260 of the translation member. The ramped portions 324, 326 can be oriented in an oblique fashion, as illustrated. In a preferred embodiment, the grooved portions 330, 332 are dovetail grooves configured and dimensioned to hold the angled surfaces 258, 260 of the translation member 218 while allowing the angles surfaces 258, 260 to slide against the ramped portions 324, 326.

In an exemplary embodiment, the first ramped insert 320 should be configured and dimensioned to be engaged with the first endplate 214. In an embodiment, the first and second ramped portions 324, 326 include snap connectors 334, 336 for securing the first ramped insert 320 to the first endplate. It should be understood that the snap connectors 334, 336 are merely illustrative and that other suitable mechanisms for securing the first ramped inserted 320 with the first endplate 214 may be used.

Figure 27:
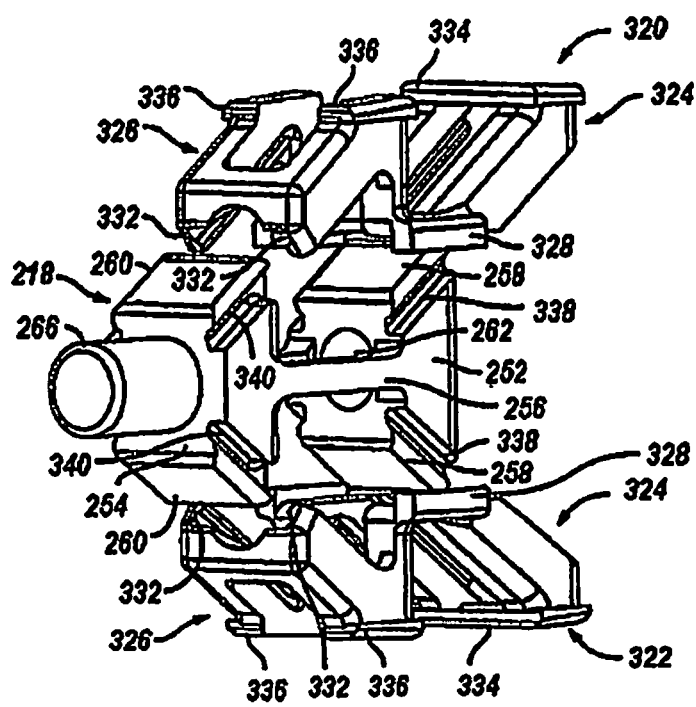
FIG. 27 is a front perspective view of the expandable fusion device of FIG. 24 showing the translation member and the ramped insert.

Referring to FIGS. 24-27, in an exemplary embodiment, the translation member 218 is sized to be received within the central opening of the body portion 212 and includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260 configured and dimensioned to engage the grooved portions 330, 332 of the first and second ramped inserts 320, 322. In one embodiment, the angled surfaces 258, 260 include corresponding grooved portions 338, 340, as best seen in FIG. 27, that slidingly engaged the grooved portions 330, 332 of the first and second ramped inserts 320, 322.

In one embodiment, the expansion portion 252 includes an opening 262, which is sized to receive a portion of the actuation member 220, and the expansion portion 262 includes a nose 266, which is received within an opening 272 in the first end 234 of the body portion 212 to stabilize the translation member 218 in the central opening of the body portion 212. In an embodiment, the nose 266 is integral with the expansion portion 262. In an embodiment (shown on FIGS. 16 and 18-20), the nose 266 is threadingly engaged with the expansion portion 262. In an embodiment, the translation member 218 includes a locking mechanism 274 to engage the actuation member 220, as illustrated in FIGS. 16-20. However, it should be understood that other suitable mechanisms may be used to secure the actuation member 220 within the translation member 218. For example, the actuation member 220 may include an extension 287 having a lip portion 286 (shown on FIGS. 16 and 18-20) that engages the expansion portion 262. The extension 287 may, for example, be configured to flex inwardly reducing its diameter when received in the opening 262. Once the lip portion 286 of the extension 287 is advanced beyond the end of the opening 262, the extension portion 287 will return back to its original diameter and the lip portion 286 will engage the expansion portion 260.

The expandable fusion device 210 of FIGS. 24-27 can be inserted into the intervertebral space in a manner similar to that the previously described with respect to FIGS. 15-20. After insertion, the expandable fusion device 210 of FIGS. 24-27 can be expanded into the expanded position, as best seen in FIGS. 24 and 25. To expand the fusion device 210, an instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a first direction, the actuation member 220 and the translation member 218 move with respect to the body portion 212 toward the first end 222 of the body portion 212. In another exemplary embodiment, the actuation member 220 is moved in a linear direction with the ratchet teeth engaging as means for controlling the movement of the actuation member 220 and the translation member 218. As the translation member 218 moves, the angled surfaces 258, 260 of the expansion portions 252, 254 push against the ramped portions 324, 326 of the first and second ramped inserts 320, 322 while riding along the grooved portions 330, 332, thus pushing first and second ramped inserts 320, 322 outwardly. Because the first and second ramped inserts 320, 322 are engaged with the endplates 214, 216, the endplates 214, 216 are also pushed outwardly into the expanded position.

After expansion, the expandable fusion device 210 can be contracted back to the unexpanded configuration. To contract the fusion device 210, the instrument is engaged with recess 284 in the actuation member 220. The instrument is used to rotate actuation member 220. As discussed above, actuation member 220 can be threadingly engaging body portion 212 and is engaged with translation member 218; thus, as the actuation member 220 is rotated in a second direction, opposite the first direction, the actuation member 220 and translation member 218 move with respect to the body portion 212 toward the second end 226 of the body portion 212. As the translation member 218 moves, the angled surfaces 258, 260 of the translation member 218 ride along the grooved portions 330, 332 pulling the first and second ramped inserts 320, 322 and thus, the endplates 214, 216 inwardly into the unexpanded position.

Figure 28:
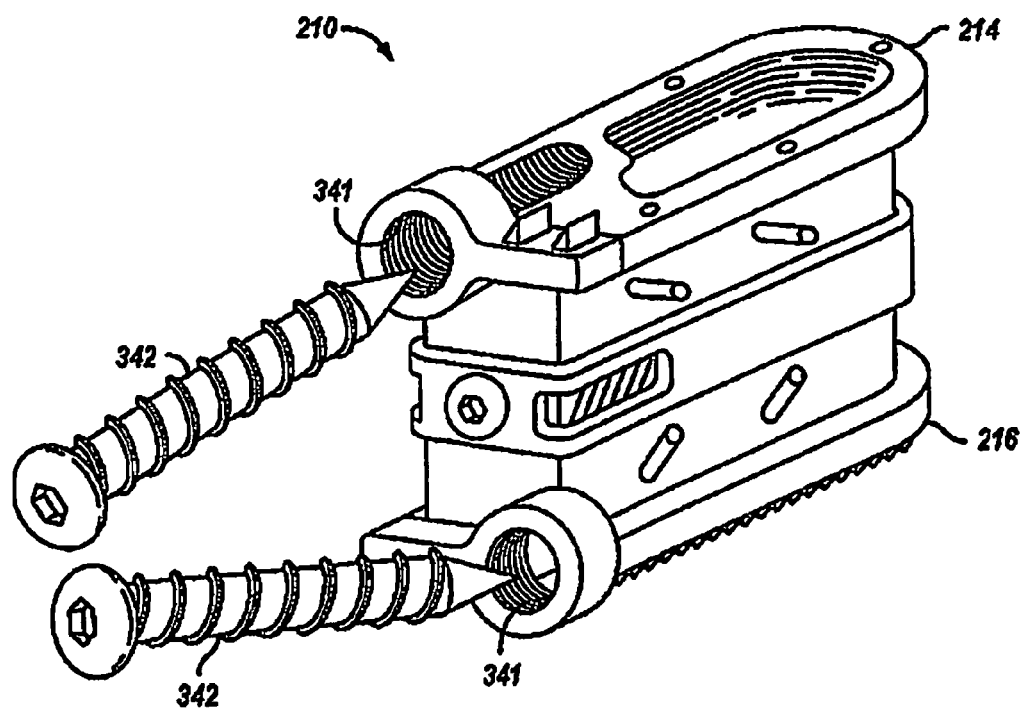
FIG. 28 is a rear perspective of another embodiment of an expandable fusion device with the endplates having a threaded hole.

Referring now to FIG. 28, an alternative embodiment of the fusion device 210 is shown. In an exemplary embodiment, the first endplate 214 and the second endplate 216 each include additional geometry to help securely hold the endplates 214, 216 in place. In an embodiment, the first endplate 214 and/or the second endplate 216 include threaded holes 341 through which the fasteners, such as screws 342, may be inserted. In an embodiment, the threaded holes 341 penetrate through the first endplate 214 and/or the second endplate 216 in an oblique fashion. It is contemplated that the screws 342 may inserted through the threaded holes 341 and into adjacent vertebral bodies 202, 203, to further secure the first endplate 214 and the second endplate 216 to the vertebral bodies 202, 203. In some embodiments, these fasteners may be removed once a more long-term interface has been established, or alternatively the fasteners may remain in place indefinitely or until the fusion device 210 needs adjustment and/or replacement.

Figure 29:
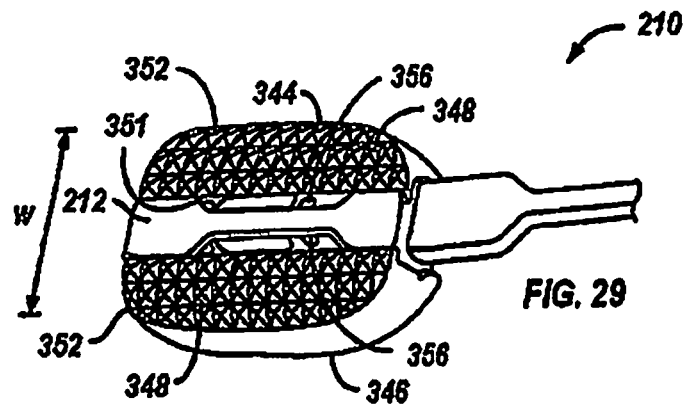
FIG. 29 is a top view of another embodiment of an expandable fusion device shown in an unexpanded position.
Figure 30:
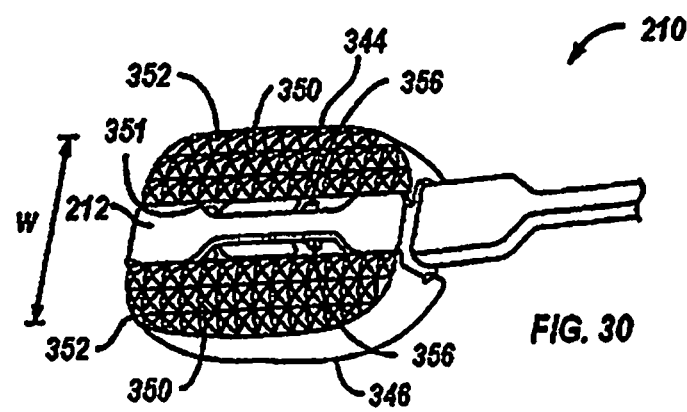
FIG. 30 is a bottom view of the expandable fusion device of FIG. 29.
Figure 31:
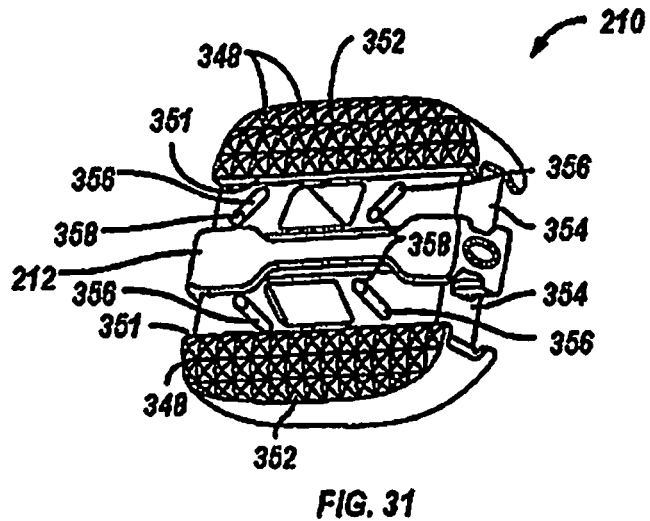
FIG. 31 is top view of the expandable fusion device of FIG. 29 shown in an expanded position.

With reference now FIGS. 29-31, an alternative embodiment of the fusion device 210 is shown that expands laterally. Lateral expansion maximizes coverage of the intravertebral disc space for wider load distribution and stability providing a rigid foundation for fusion. In one embodiment, the fusion device 210 includes body portion 212, first endplate 344, and second endplate 346.

Figure 32:
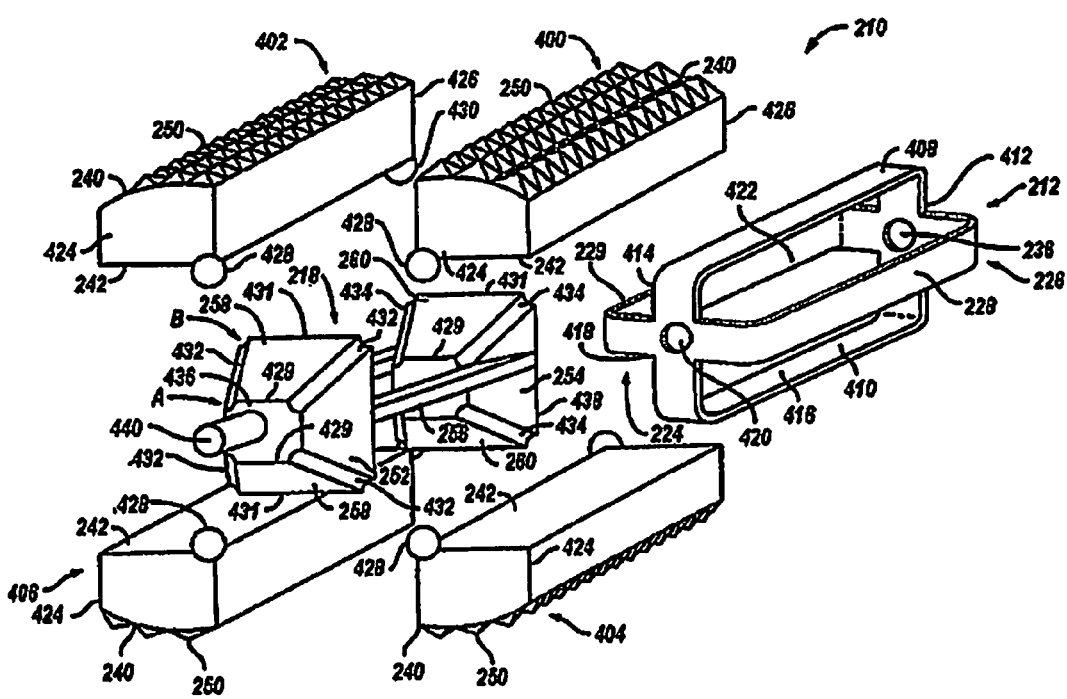
FIG. 32 is an exploded perspective view of another embodiment of an expandable fusion device.
Figure 33:
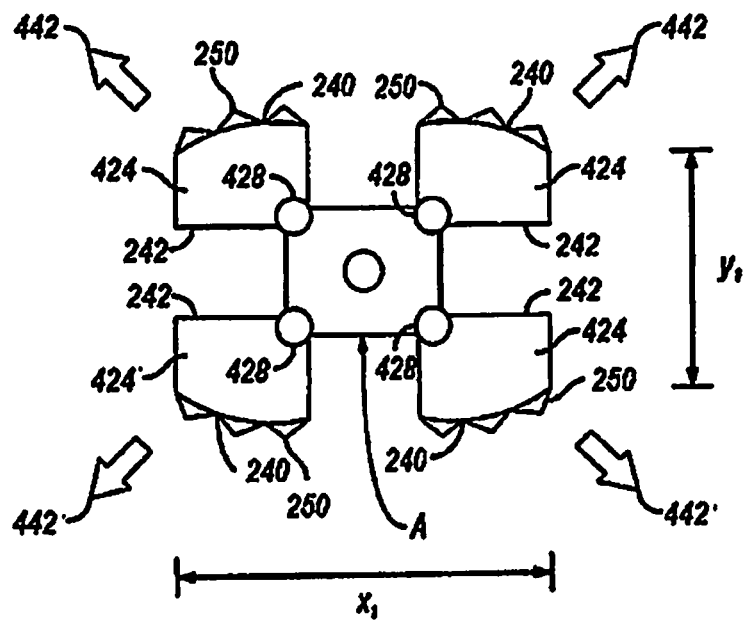
FIG. 33 is an end view of the expandable fusion device of FIG. 32 in an unexpanded position.

Although the following discussion relates to the first endplate 344, it should be understood that it also equally applies to the second endplate 346 as the second endplate 346 is substantially identical to the first endplate 344 in embodiments of the present invention. Turning now to FIGS. 31-33, in an exemplary embodiment, the first endplate 344 has an upper surface 348, a lower surface 350, and an inner surface 351 facing the body portion 212. It is contemplated that the upper surface 348 will engage adjacent vertebral body 202 (seen on FIG. 15) and the lower surface 350 will engage adjacent vertebral body 203 (seen on FIG. 15). In one embodiment, the upper surface 348 and the lower surface 350 are each flat and generally planar to allow the upper surface 348 to engage with the adjacent vertebral body 203. Alternatively, the upper surface 348 and/or the lower surface 350 can be curved convexly or concavely to allow for a greater or lesser degree of engagement with the adjacent vertebral bodies 202, 203. It is also contemplated that the upper surface 348 and/or the lower surface 350 can be generally planar but includes a generally straight ramped surface or a curved ramped surface. The ramped surface allows for engagement with the adjacent vertebral body 202 and/or the adjacent vertebral body 203 in a lordotic fashion. In an exemplary embodiment, the upper surface 348 and/or lower surface 350 includes textures 352 to aid in gripping the adjacent vertebral bodies. Although not limited to the following, the texturing can include teeth, ridges, friction increasing elements, keels, or gripping or purchasing projections.

In one embodiment, the inner surface 351 includes at least one extension 354 extending along at least a portion of the inner surface 351. In an exemplary embodiment, the extension 354 can extend along a substantial portion of the inner surface 354, including, along each side of the endplate 344 and along the front end of the endplate 214. While not illustrated, the inner surface may include ramped surfaces and grooved portions in an exemplary embodiment. It is contemplated that the ramped surfaces and/or grooved portions may be similar to the ramped surfaces 246, 248 and grooved portion 247, 249 in extension 244 shown on FIGS. 18-20. In an embodiment, the extension 354 may include slots 356 oriented in an oblique fashion through which pins 358 may be inserted.

While not illustrated, the fusion device 210 further includes features to effectuate the lateral expansion of the first and second endplates 344, 346. In one embodiment, the fusion device 210 using a ramping system—similar to the system illustrated in FIGS. 16 and 18-20—for expanding the first and second endplates 344, 346. In an exemplary embodiment, the fusion device 210 further includes a translation member and actuation member, such as translation member 218 and actuation member 220 shown on FIGS. 16 and 18-20. It is contemplated that the translation member may include angled surfaces that push against ramped surfaces in the extension 354, expanding the first and second endplates 344, 346 outwardly and away from the body portion 212. In an embodiment, pins 356 disposed through the slots 354 may be retained in the translation member. In an alternative embodiment, dovetailing may be used for engagement of the angled surfaces and ramped surfaces. It should be understood that the translation member and actuation member in this embodiment may be similar to the translation member 218 and actuation member 220 described above with respect FIGS. 15-20. In another embodiment, the fusion device 210 further includes first and second ramped inserts that are secured within the first and second endplates 344, 346. The first and second ramped inserts may be similar to the first and second ramped inserts 320, 322 described above with respect to FIGS. 24-27. It is contemplated that angled surfaces in the translation member may push against ramped surfaces in the ramped inserts pushing the ramped inserts outwardly. Because of their engagement with the first and second endplates 344, 346, the first and second endplates 344, 346 may thus be expanded outwardly. In this manner, the first and second endplates 344, 346 may be laterally expanded away from the body portion 212. It should be understood that other suitable techniques may also be used to effectuate this lateral expansion.

With reference to FIG. 32, an exploded perspective view of another embodiment of fusion device 210 is shown. In an exemplary embodiment, the fusion device 210 includes a body portion 212, a first endplate 400, a second endplate 402, a third endplate 404, a fourth endplate 406, and a translation member 218. In this embodiment, the fusion device 210 is configured to expand both vertically and laterally.

In an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The body portion 212 further includes a top side portion 408 connecting the first end 224 and the second end 226, and a bottom side portion 410 on the opposing side of the body portion 212 connecting the first end 224 and the second end 226. The body portion 212 further includes first gap 412 between the top side portion 408 and the first side portion 228, which is sized to receive at least a portion of the first endplate 400. The body portion 212 further includes second gap 414 between the top side portion 408 and the second side portion 229, which is sized to receive at least a portion of the second endplate 402. The body portion 212 further includes third gap 416 between the bottom side portion 410 and the first side portion 228, which is sized to receive at least a portion of the third endplate 404. The body portion 212 further includes fourth gap 418 between the bottom side portion 410 and the second side portion 229, which is sized to receive at least a portion of the fourth endplate 406.

The first end 224 of the body portion 212, in an exemplary embodiment, includes an opening 420. The opening 420 extends from the first end 224 of the body portion 212 into a central opening 422. In one embodiment, the central opening 422 is sized to receive the translation member 218. The second end 226 of the body portion 212, in an exemplary embodiment, includes an opening 236, which extends from the second end 226 of the body portion 212 into the central opening 422.

Figure 34:
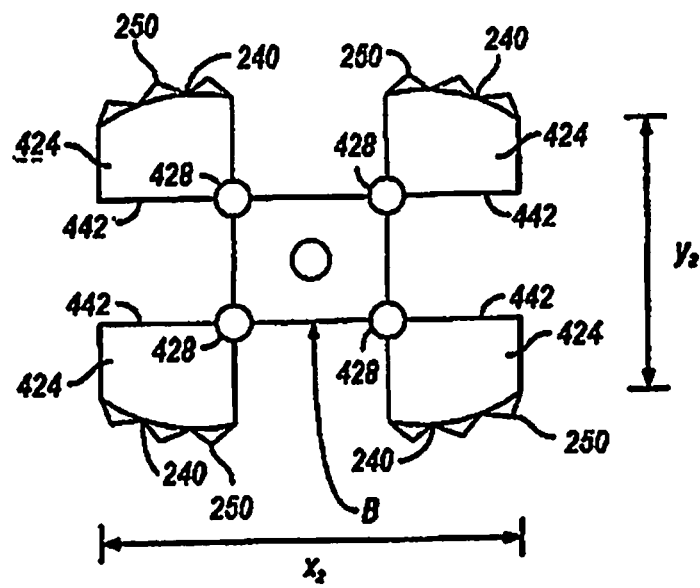
FIG. 34 is an end view of the expandable fusion device of FIG. 32 in an expanded position.

Although the following discussion relates to the first endplate 400, it should be understood that it also equally applies to the second endplate 402, the third endplate 404, and the fourth endplate 406, as these endplates 402, 404, 406 are substantially identical to the first endplate 400 in embodiments of the present invention. Turning now to FIGS. 32-34, in an exemplary embodiment, the first endplate 214 has a first end 424 and a second end 426. The first endplate further includes an upper surface 240 connecting the first end 424 and the second end 426 and a lower surface 442 on an opposing side of the endplate 400 connecting the first end 424 and the second end 426. While not illustrated, the first endplate 214 may include a through opening sized to receive bone graft or similar bone growth inducing material and further allow the bone graft or similar bone growth inducing material to be packed in the central opening 422 in the body portion 212.

In one embodiment, the lower surface 242 includes at least one first retaining socket 428 on the lower surface 242. In an exemplary embodiment, the lower surface 242 includes a first retaining socket 428 at the interior corner of the intersection of the first end 424 and the lower surface 242, and a second retaining socket 430 at the interior corner of the intersection of the first end 424 and the lower surface 242.

Referring now to FIGS. 32-34, in one embodiment, the upper surface 240 of the first endplate 400 is curved convexly. Alternatively, the upper surface 240 is flat or curved concavely to allow for a greater or lesser degree of engagement with the adjacent vertebral body 202. It is also contemplated that the upper surface 240 can be generally planar but includes a generally straight ramped surface or a curved ramped surface. The ramped surface allows for engagement with the adjacent vertebral body 202 in a lordotic fashion. In an exemplary embodiment, the upper surface 240 includes texturing 250 to aid in gripping the adjacent vertebral bodies. Although not limited to the following, the texturing can include teeth, ridges, friction increasing elements, keels, or gripping or purchasing projections.

With reference to FIG. 32, in an exemplary embodiment, the translation member 218 is sized to be received within the central opening 422 of the body portion 212. The translation member 218 should be sized to allow longitudinal translation within the central opening 422. In an embodiment, the translation member 218 includes at least a first expansion portion 252. In another embodiment, the translation member 218 includes a first expansion portion 252 and a second expansion portion 254, the expansion portions 252, 254 being connected together via a bridge portion 256. It is also contemplated that there may be more than two expansion portions where each of the expansion portions is connected by a bridge portion. The expansion portions 252, 254 each have angled surfaces 258, 260. In an embodiment, the angles surfaces 258, 260 each comprise first end 429 and second end 431 with second end 431 being wider than the first end 429. In an exemplary embodiment, the expansion portions 252, 254 include grooved portions 432, 434 on the edges of at least two sides (e.g., the lateral sides) of the angled surfaces 258, 260. The grooved portions 432, 434 are configured and dimensioned to engage the first and second retaining sockets 428, 430 on the endplates 400, 402, 404, 406. In an exemplary embodiment, the grooved portions 432, 434 retain the first and second retaining sockets 428, 430 in sliding engagement.

In one embodiment, the translation member 218 includes a first end 436 and a second end 438. The first end 436 of the translation member includes an extension 440 sized to be received within the opening 420 in the first end 224 of the body portion 212. While not illustrated, the second end 438 also can include a similar extension sized to be received within opening 232 in the second end 226 of the body portion 212.

The expandable fusion device 210 of FIGS. 32-34 can be inserted into the intervertebral space in a manner similar to that the previously described with respect to FIGS. 15-20. After insertion, the expandable fusion device 210 of FIGS. 32-34 can be expanded into the expanded position. As previously mentioned, the fusion device 210 shown on FIGS. 32-34 expands both vertically and laterally. To expand the fusion device 210, the translation member 218 can be moved with respect to the body portion 212 toward the first end 224 of the body portion. An instrument can be used, in an exemplary embodiment. As the translation member 218 moves, the first retaining socket 428 and the second retaining socket 430 ride along the grooved portions 432, 434 of the expansion portions 252, 254 pushing the endplates 400, 402, 404, 406 outwardly in the direction indicated by arrows 442. In an embodiment, the endplates 400, 402, 404, 406 move outwardly in an oblique fashion to expand the fusion device 210 both vertically and laterally. The expanded configuration of the expansion device 210 is best seen in FIG. 34.

After expansion, the expandable fusion device 210 can be contracted back to the unexpanded configuration. The unexpanded configuration of the fusion device 210 is best seen in FIG. 34. To contract the fusion device 210, the translation member 218 is moved with respect to the body portion 212 toward the second end 226 of the body portion 212. As the translation member 218 moves, the first retaining socket 428 and the second retaining socket 430 ride along the grooved portions 432, 434 of the expansion portions 252, 254 pulling the endplates 400, 402, 404, 406 inwardly in a direction opposite that indicated by arrows 442. In an embodiment, the endplates 400, 402, 404, 406 move inwardly in an oblique fashion to contract the fusion device 210 both vertically and laterally. The unexpanded configuration of the expansion device 210 is best seen in FIG. 33.

Figure 35:
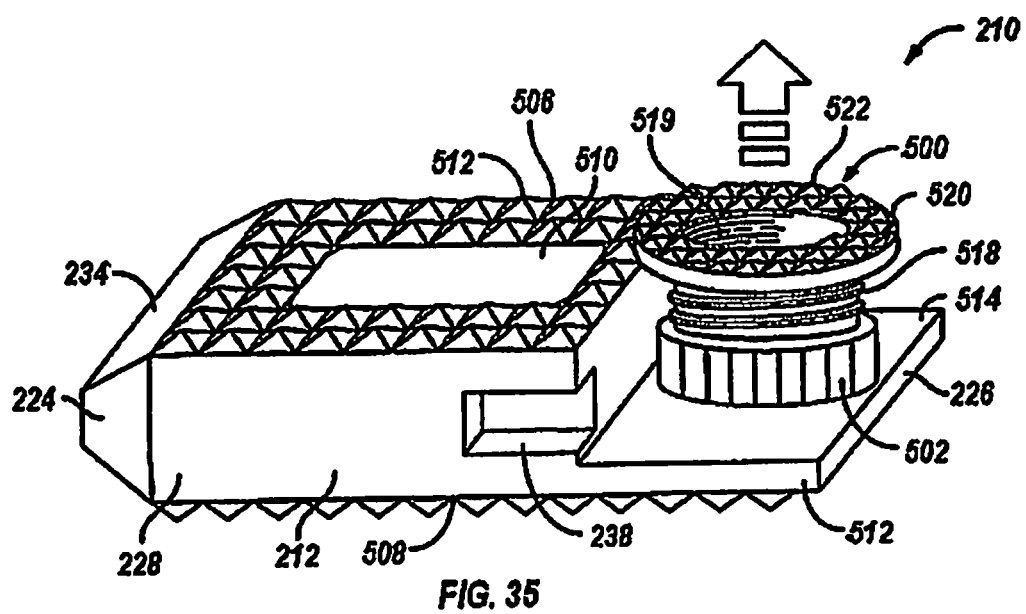
FIG. 35 is a perspective view of another embodiment of an expandable fusion device.
Figure 36:
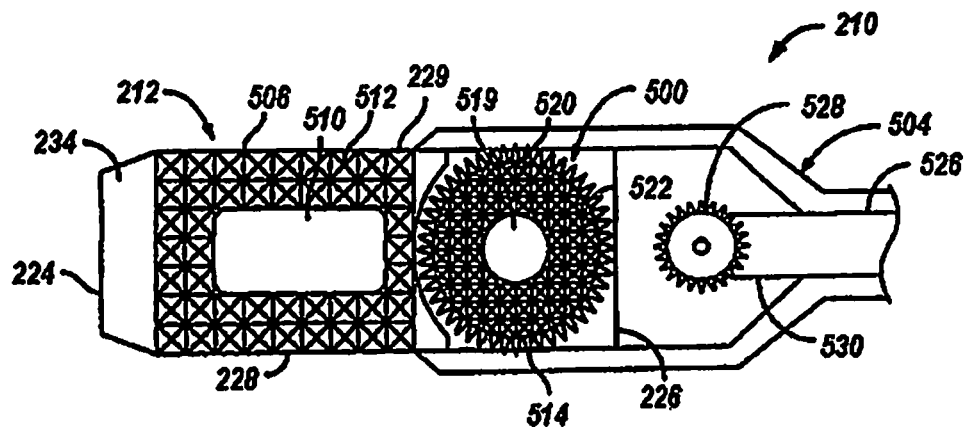
FIG. 36 is a top view of the expandable fusion device of FIG. 35.

With reference to FIGS. 35-36, another embodiment of expandable fusion device 210 is shown. In an exemplary embodiment, the fusion device 210 includes a body portion 212, a vertically expanding plate 500, and a gear 502. In this embodiment, a portion of the fusion device 210 is configured to expand vertically in at least one direction. In an exemplary embodiment, the vertically expanding plate 500 is configured to expand outwardly from the body portion 212. It is contemplated that an expandable fusion device 210 may be used to correct spinal curvature due to, for example, scoliosis, lordosis, and the like.

In an exemplary embodiment, the body portion 212 has a first end 224, a second end 226, a first side portion 228 connecting the first end 224 and the second end 226, and a second side portion 229 on the opposing side of the body portion 212 connecting the first end 224 and the second end 226. The first end 224 of the body portion 212, in an exemplary embodiment, includes at least one angled surface 234, but can include multiple angled surfaces. The angled surface 234 can serve to distract the adjacent vertebral bodies when the fusion device 210 is inserted into an intervertebral space. In another preferred embodiment, it is contemplated that there are at least two opposing angled surfaces forming a generally wedge shaped to distract the adjacent vertebral bodies when the fusion device 210 is inserted into an intervertebral space. In yet another preferred embodiment, first side portion 228 and second side portion 229 each include a recess 238 located towards the second end 226 of the body portion 212. The recess 238 is configured and dimensioned to receive an insertion instrument 504 that assists in the insertion of the fusion device 210 into an intervertebral space.

In an exemplary embodiment, the body portion 212 includes an upper engagement surface 506 extending from the first end 224 towards the second end 226, and a lower engagement surface 508 extending between the first end 224 and the second end 226. In an embodiment, the upper engagement surface 506 has a through opening 510. Although not illustrated, the lower engagement surface 508 may have a through opening that is similar to through opening 510. The through opening 510, in an exemplary embodiment, is sized to receive bone graft or similar bone growth inducing material and further allow the bone graft or similar bone growth inducing material to be packed in the central opening in the body portion 212. In an embodiment, at least a portion of the body portion 212 is removed to form a landing 512 in the body portion 212. In an exemplary embodiment, a portion of the upper engagement surface 506 and the second end 226 are removed to form the landing 512 having an upper surface 514. While not illustrated, a portion of the lower engagement surface 508 and the second end 226 may be cut away, in an alternative embodiment, to form the landing 512.

In one embodiment, the upper engagement surface 506 and the lower engagement surface 508 are flat and generally planar to allow engagement surfaces 506 to engage with the adjacent vertebral body 202 and the lower engagement surface 508 to engage with the adjacent vertebral body 203. Alternatively, the upper engagement surface 506 and/or the lower engagement surface 508 can be curved convexly or concavely to allow for a greater or lesser degree of engagement with the adjacent vertebral bodies 202, 203. In an exemplary embodiment, the upper engagement surface 506 and/or the lower engagement surface includes texturing 512 to aid in gripping the adjacent vertebral bodies. Although not limited to the following, the texturing can include teeth, ridges, friction increasing elements, keels, or gripping or purchasing projections.

In an exemplary embodiment, vertically expanding plate 500 is coupled to an end of threaded bolt 518, which is coupled to the gear 502. In one embodiment, the threaded bolt 518 is in threaded engagement with the gear 502. In an alternative embodiment, a bolt having ratchet teeth may be used instead of threaded bolt 518. In an embodiment, the gear 502 is coupled to the landing 512. In one embodiment, the gear 502 is rotatably coupled to the landing 512.

Figure 37:
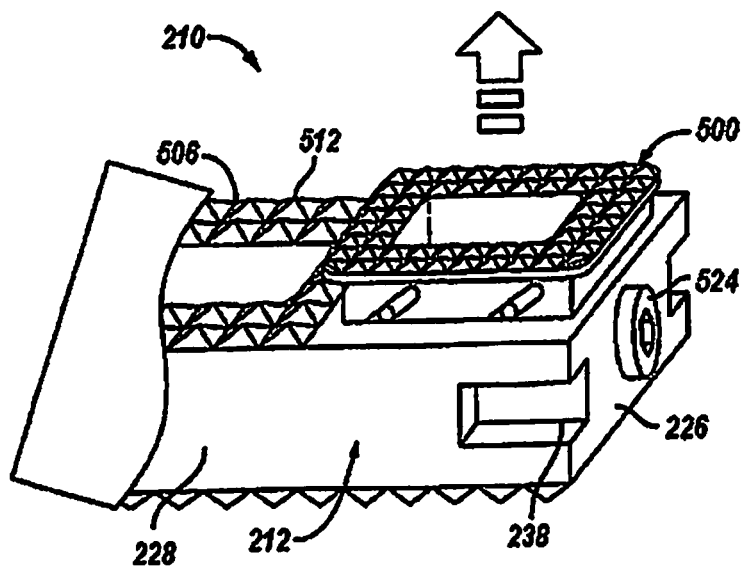
FIG. 37 is a perspective view of the expandable fusion device of FIG. 35 with a closed end.

The vertically expanding plate 500 includes a throughbore 519 and an upper surface 520. In one embodiment, the vertically expanding plate 500 is generally circular in shape. Other suitable configurations of the expanding plate 500 may also be suitable. In an embodiment, the vertically expanding plate may be generally rectangular in shape with rounded corners, as best seen in FIG. 37. In one embodiment, the vertically expanding plate 500 is flat and generally planar to allow upper surface 520 to engage with the adjacent vertebral body 202. Alternatively, the upper surface 520 can be curved convexly or concavely to allow for a greater or lesser degree of engagement with the adjacent vertebral bodies. In an exemplary embodiment, the upper surface 520 includes texturing 522 to aid in gripping the adjacent vertebral bodies. Although not limited to the following, the texturing can include teeth, ridges, friction increasing elements, keels, or gripping or purchasing projections.

With reference to FIG. 37, an alternative embodiment of the expandable fusion device 210 of FIGS. 35-36 is shown. In this embodiment, the gear 502 is enclosed within the body portion 212 towards the second end 226 of the body portion 212 with the vertically expanding plate 500 disposed at or above the upper engagement surface 506 of the body portion 212. In an embodiment, the vertically expanding plate 500 is positioned towards the second end 226 of the body portion 212. While not illustrated, the threaded bolt 518 extends through the upper engagement surface 506 and couples the vertically expanding plate 500 and the gear 502. An actuator screw 524 extends through the first end 224 of the body portion 212 to engage the gear 502.

Figure 38:
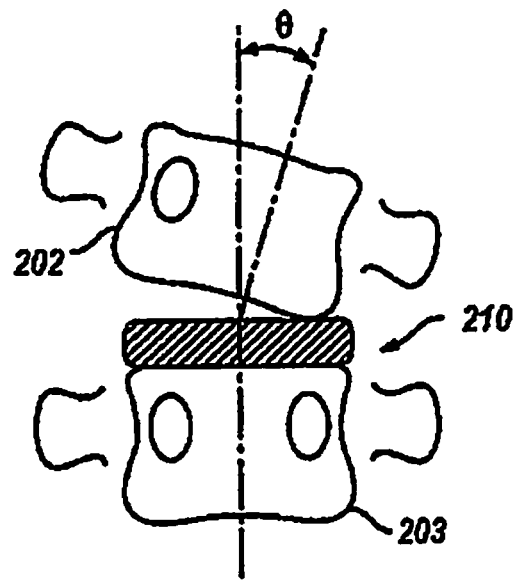
FIG. 38 is a front view of the expandable fusion device of FIG. 37 shown between adjacent vertebrae in an unexpanded position.
Figure 39:
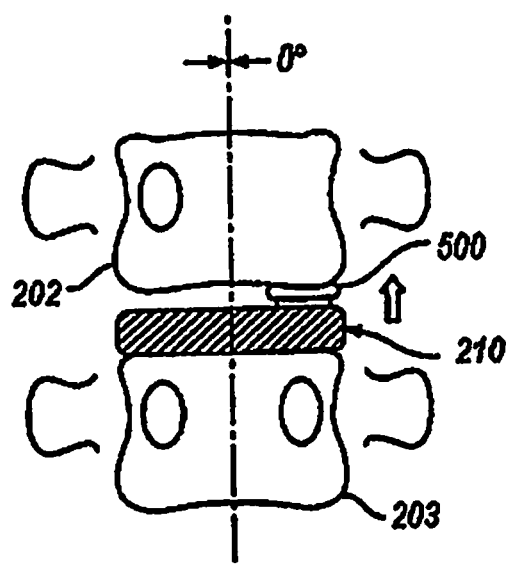
FIG. 39 is a front view of the expandable fusion device of FIG. 37 shown between adjacent vertebrae in an expanded position.

The expandable fusion device 210 of FIGS. 35-37 can be inserted in the intervertebral space in a manner similar to that the previously described with respect to FIGS. 15-20. FIG. 38 illustrates the expandable fusion device 210 of FIG. 37 between adjacent vertebral bodies 202, 203 in an unexpanded position. After insertion, the expandable fusion device 210 of FIGS. 35-37 can be expanded into the expanded position. As previously mentioned, a portion of the fusion device shown on FIGS. 35-37 expands vertically in at least one direction. To partially expand the fusion device 210, the gear 502 can be rotated in a first direction. An instrument 526 having a gear 528 disposed on a distal end 530 of the instrument may be used to rotate the gear 502, as best seen on FIG. 36. In another embodiment, an instrument (not illustrated) may be used to rotate actuation member 524 in a first direction. As discussed above, the actuation member 524 is engaged with gear 502; thus, as the actuation member 524 is rotated in first direction, the gear 502 rotated in a first direction. The embodiment with the actuation member 524 is best seen in FIG. 37. As the gear 502 rotates, the threaded bolt 518 extends outward from the gear 502, thus extending the laterally expanding plate 500 outward from the body portion 212. FIG. 39 illustrates the expandable fusion device 210 of FIG. 37 in an expanded position.

After expansion, the expandable fusion device 210 can be contracted back to the unexpanded position. The unexpanded position of the fusion device 210 is best seen in FIG. 38. To contract the fusion device 210, the gear 502 is rotated in a second direction that is opposite the first direction. The instrument 526 with the gear 528 may be used to rotate the gear 502. Alternatively, an instrument may be used to rotate the actuation member 524 to turn the gear 502 in the second direction. As the gear 502 rotates in the second direction, the threaded bolt 518 retracts pulling the laterally expanding plate 500 inward into the unexpanded position.

Additional Embodiments for the Expandable Fusion Device

In some embodiments, the fusion devices 210 can include additional features that provide additional benefits such as preventing screw loosening and added stability. These embodiments are discussed below.

Figure 40:
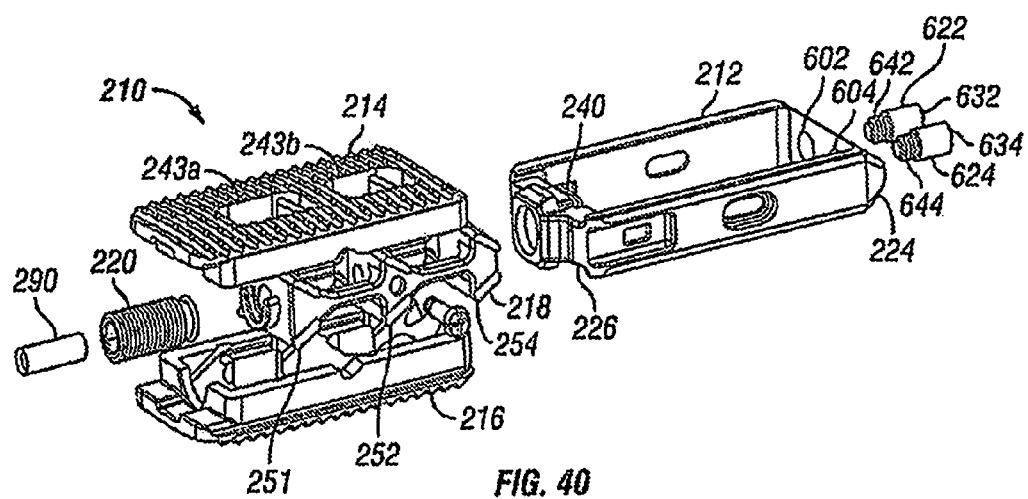
FIG. 40 is an exploded view of an alternative fusion device.
Figure 41:
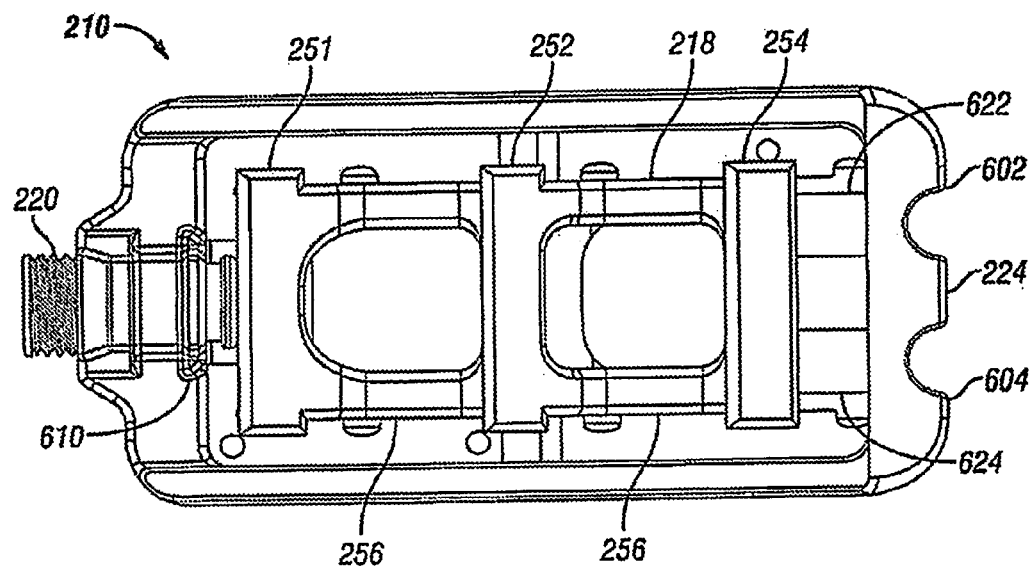
FIG. 41 is a top view of the device in FIG. 40 with a first endplate removed.

FIGS. 40 and 41 show different views of a fusion device 210 including an advantageous interference nut 610 and stabilization members 622, 624 according to some embodiments. The fusion device 210 includes many features similar to the above-described devices, including a body portion 212, a first endplate 214, a second endplate 216, a translation member 218, and an actuation member 220. The first endplate 214 can include a pair of openings 243a and 243b through which bone graft material can be received or deposited. Likewise, the second endplate 16 can have similar openings, although they are not shown from the illustrated viewpoints. In addition to these features, the fusion device 210 includes a novel interference nut 610 that is operably attached to a rear section of the body portion 212, as well as a pair of stabilization members 622, 624.

FIG. 40 illustrates an exploded view of the alternative fusion device 210, while FIG. 41 shows a top view of the same device with the first endplate 214 removed. As shown in both views, the translation member 218 includes three expansion portions 251, 252, and 254, which are connected via bridge portions 256. The expansion portions 251, 252, and 254 each have angled surfaces that are configured to engage grooved portions of the first and second endplates 214 and 216. In some embodiments, the angled surfaces are of similar angles, while in other embodiments, the angled surfaces are of different angles. Advantageously, by providing at least three expansion portions 251, 252 and 254, this allows for an even expansion along a majority of the length of the body portion 212 of the fusion device 210.

The translation member 218 is received in the central opening of the body portion 212. The body portion 212 can include a first end 224 and a second end 226. In some embodiments, the first end 224 includes one or more apertures 602, 604 as shown in FIGS. 40 and 41. These apertures 602, 604 advantageously receive one or more stabilization members 622, 624.

In some embodiments, the stabilization members 622, 624 each include a first substantially smooth portion 632, 634 and a second threaded portion 634, 644. The stabilization members 622, 624 can be inserted through the apertures 602, 604 of the body portion 212, with the threaded portions 634, 644 serving as the leading end that enters the apertures. After passing through the apertures 602, 604 of the body portion 212, the stabilization members 622, 624 can come into contact with a side of the translation member 218. In some embodiments, the threaded portions 634, 644 of the stabilization members 622, 624 can be threaded into mateable threaded surfaces of the translation member 218. Advantageously, by using a pair of stabilization members 622, 624 as shown in FIGS. 40 and 41 on a first end of the body portion 212, this serves to prevent rocking of the body portion 212 during expansion and contraction of the device 210.

While the illustrated embodiment in FIGS. 40 and 41 show a pair of stabilization members 622, 624, in other embodiments, a single stabilization member or more than two stabilization members can be used to assist in preventing rocking of the body portion 212. In addition, while the stabilization members 622, 624 are illustrated as having a substantially cylindrical surface section, in other embodiments, the stabilization members 622, 624 can assume other shapes and geometries. For example, in other embodiments, the stabilization members 622, 624 can have a surface that includes at least one edge or corner.

As shown in FIGS. 40 and 41, the body portion 212 also includes an interference nut 610 that is positioned within a rear section of the body portion 212. In some embodiments, the interference nut 610 is separate and removable from the body portion 212, while in other embodiments, the interference nut 610 is not removable from the body portion 212. In some embodiments, the interference nut 610 comprises a square nut that is operably connected to a rear section of the body portion 212. The interference nut 610 can be mateably connected to a rear of the body portion 212, for example, via a dove-tail type cut that encapsulates the interference nut. The interference nut 610 can be advantageously formed of a biocompatible material. In some embodiments, the interference nut 610 is formed of PEEK.

The interference nut 610 can include a hole (not shown) that is capable of receiving the actuation member 220 therethrough. The actuation member 220, which can comprise a threaded set screw, passes through the interference nut 610 and into contact with the translation member 218, as best shown in FIG. 41. Advantageously, the interference nut 610 serves to add drag to the actuation member 220 as it passes therethrough, thereby establishing an interference fit. By providing an interference fit, the risk of the actuation member 220 being loosened prior to or during use is minimized.

Figure 42:
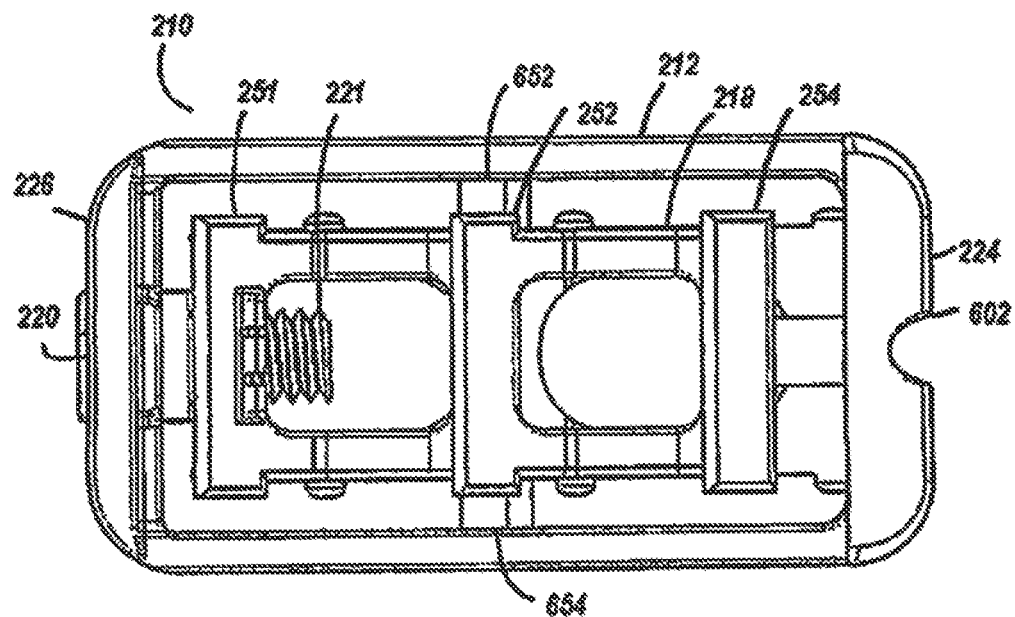
FIG. 42 is a top view of the alternative fusion device having side stabilization members.
Figure 43:
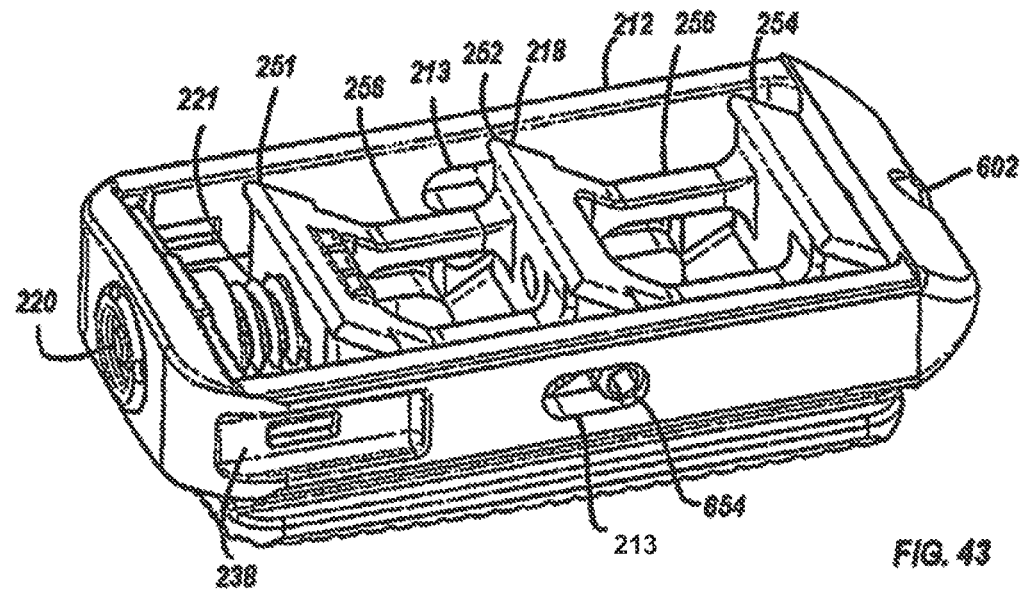
FIG. 43 is a perspective view of the device in FIG. 42.
Figure 44:
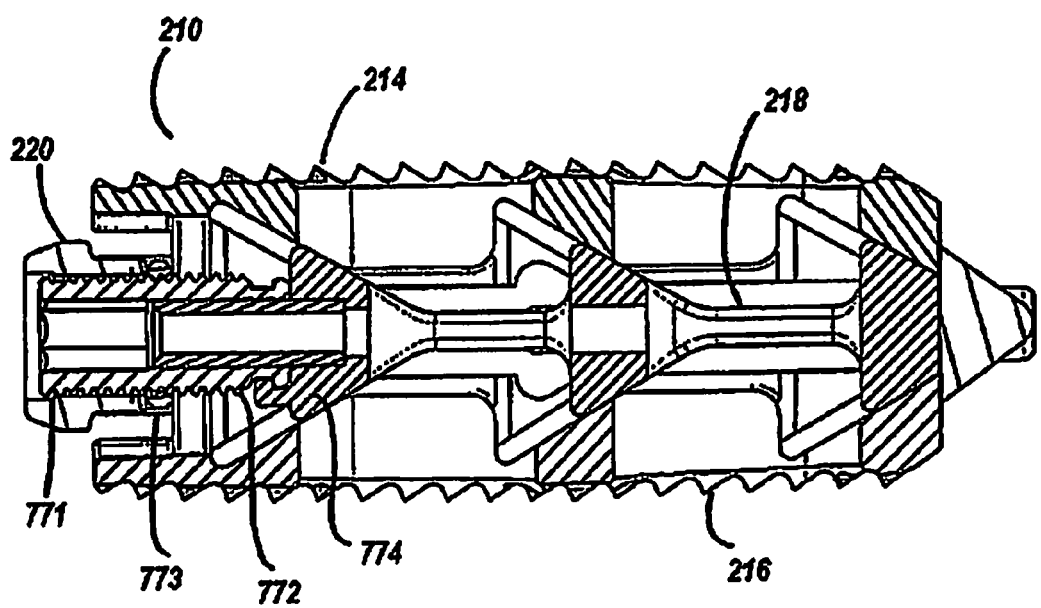
FIG. 44 is a side cross-sectional view of the device in FIG. 42.

FIGS. 42-44 show different views of an alternative fusion device 210 including novel side stabilization members 652, 654 and a low profile actuation member 220. The fusion device 210 includes many features similar to the above-described devices, including a body portion 212, a translation member 218, and an actuation member 220. The fusion device 210 can also include a first endplate 214 and a second endplate 216 for contacting vertebral surfaces, as best shown in FIG. 44. Both the first endplate 214 and second endplate 216 can include a pair of openings through which bone graft material can be received or deposited. In addition to these features, the fusion device 210 includes novel side stabilization members 652, 654 that are introduced through side slots 213 of the body portion 212. The fusion device 210 also includes a configuration that allows the actuation member 220 to be of low profile, as shown in FIG. 42.

FIG. 42 illustrates a top view of the alternative fusion device 210 having side stabilization members with the first endplate 214 removed, while FIG. 43 illustrates a perspective view of the same device. FIG. 44 illustrates a side cross-sectional view of the alternative fusion device 210 having side stabilization members. As shown in all three views, the translation member 218 includes three expansion portions 251, 252, and 254, which are connected via bridge portions 256. The expansion portions 251, 252, and 254 each have angled surfaces that are configured to engage grooved portions of the first and second endplates 214 and 216. In some embodiments, the angled surfaces are of similar angles, while in other embodiments, the angled surfaces can be of different angles. Advantageously, by providing at least three expansion portions 251, 252 and 254, this allows for an even expansion along a majority of the length of the body portion 212 of the fusion device 210.

The translation member 218 is received in the central opening of the body portion 212. The body portion 212 can include sidewalls that extend between the first end 224 and a second end 226. As shown in FIG. 43, each of the sidewalls can include side slots 213 for receiving one or more side stabilization members 652, 654.

In some embodiments, the side stabilization members 652, 654 are similar to the stabilization members 622, 624 (shown in FIG. 40). That is, the side stabilization members 652, 654 can include a threaded portion and a substantially smooth portion. The side stabilization members 652 can be inserted through the side slots 213 of the body portion 212 and can operably attach (e.g., via threads) to the translation member 218. Advantageously, the side slots 213 help to provide rotational stability to the translation member 218 relative to the body portion 212 prior to or during use of the fusion device 210.

In addition to providing side stabilization members, the fusion device 210 provides a configuration that includes a low profile actuation member 220. Advantageously, as shown in FIG. 42, the actuation member 220 (which can comprise a screw) can have a head portion that is substantially flush against the surface of the body portion 212, while a distal portion 221 of the actuation member 220 can extend through a wall of the translation member 218.

As shown in FIG. 44, in some embodiments, the actuation member 220 can comprise a set screw 772 accompanied by a flange 773 and an actuation element 774. The set screw 772 and actuation element 774 can both be threaded. Upon rotation of the set screw 772, the actuation element 774 is threaded forward, thereby pushing the first endplate 214 upwardly and the second endplate 216 downwardly to cause expansion of the actuation member 220. The flange 773, which can be cylindrical, advantageously resists the opposing forces as the actuation element 774 is threaded forward, thereby helping to keep the fusion device 210 in an expanded configuration. Upon reverse rotation of the set screw 772, the fusion device 210 can collapse. As shown in FIG. 44, a blocking nut 771 can be provided that is threaded onto the back side of the set screw 772 to secure the set screw into place when the device 210 is collapsed.

Figure 49:
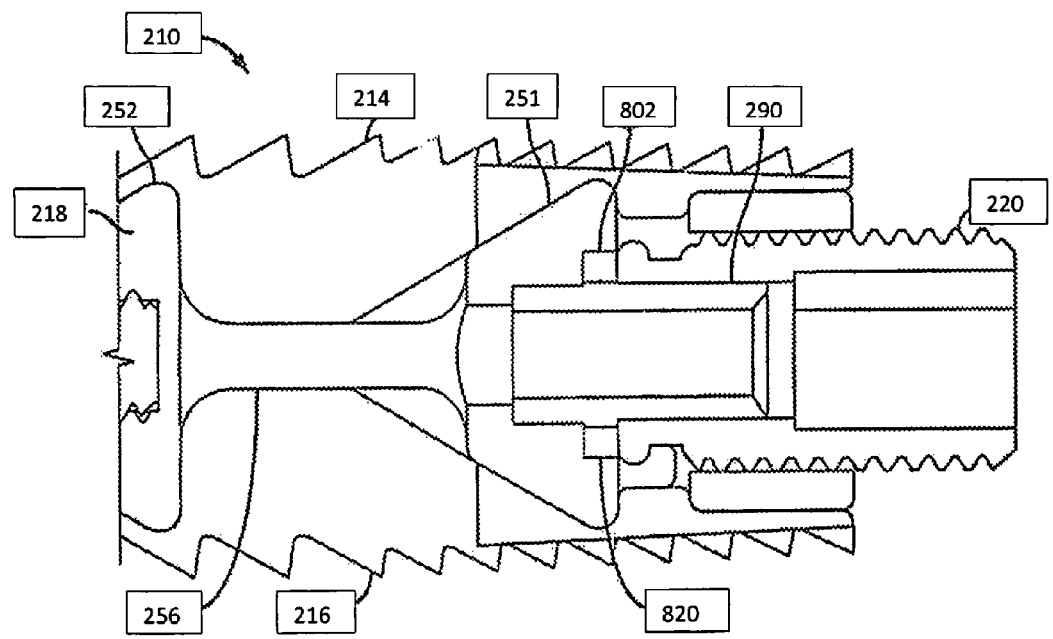
FIG. 49 is a side cross-sectional view of a portion of an alternative fusion device incorporating a ring member therein.
Figure 50:
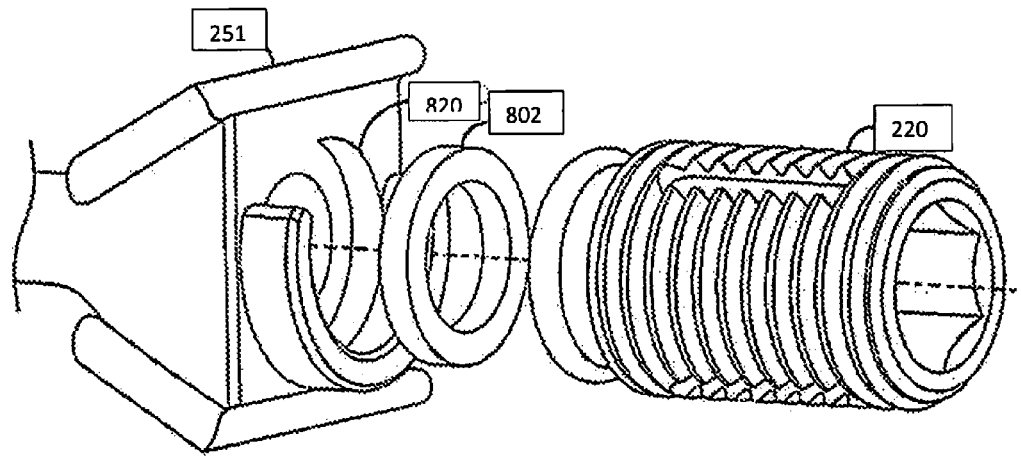
FIG. 50 is a perspective view of a portion of the alternative fusion device of FIG. 49.

Additional embodiments of an expandable fusion device 210 are shown in FIGS. 49 and 50. This fusion device 210 incorporates a ring member 802 into a pocket 820 formed in the translation member 218.

The fusion device 210 in FIGS. 49 and 50 include many features similar to the above-described devices, including a body portion 212, a first endplate 214, a second endplate 216, a translation member 218, an actuation member 220, and a pin member 290. The first endplate 214 can include one or more openings through which bone graft material can be received or deposited. Likewise, the second endplate 216 can have similar openings, although they are not shown from the illustrated viewpoints. The translation member 218 can be comprised of one or more ramped expansion portions, such as expansion portions 251 and 252, which are configured to assist in expansion and contraction of the fusion device 210, as discussed above.

In addition to these features, the fusion device 210 incorporates a ring member 802 that is positioned between the actuation member 220 and the translation member 218. In some embodiments, the ring member 802 is received in a pocket 820 that is formed in one of the expansion portions (such as expansion portion 251) of the translation member 218. As shown in FIG. 50, the ring member 802 can comprise a closed annular body that can be received in a similarly shaped recess 820 formed in the body of an expansion portion 251 of the translation member 218. Each of expansion portion 251, ring member 802 and actuation member 220 can be placed over a pin member 290.

In some embodiments, the ring member 802 can be formed of a material that is different from the translation member 218 and/or actuation member 220. For example, while in some embodiments the translation member 18 and/or actuation member 220 are comprised of a metal, such as a biocompatible stainless steel, titanium or metal alloy, the ring member 802 can be formed of a polymer such as polyether ether ketone (PEEK). The advantage of providing a PEEK ring member 802 is that a more lubricious material is positioned between the face of the actuation member 220 and the surface of the translation member 218, thereby reducing the friction between the two parts. With the PEEK ring member's 802 reduced coefficient of friction, this increases the amount of force transmitted when the actuation member 220 is screwed into the translation member 218, thereby increasing the amount of expansion force provided to the ramped translation member 218. In some embodiments, the use of a PEEK ring member between the interface of the actuation member 220 and translation member 218 increases the expansion force of the ramped translation member 218 while using the same force as would be applied if the PEEK ring member was not in place. In some embodiments, the use of a PEEK ring member between the translation member 218 and actuation member 220 provides a buffer that can prevent galling that would occur due to metal-on-metal contact between the translation member and actuation member.

In some embodiments, rather than receive an insert in the shape of ring member 802, the translation member 218 can receive an insert having a different shape. For example, the translation member 218 can include one or more recesses that accommodate a wedge-shaped PEEK member between the translation member 218 and the actuation member 220. Like the ring member 802, the wedge-shaped PEEK member can also serve as a lubricious material that reduces the friction between the translation member 218 and the actuation member 220.

In addition, in some embodiments, an insert can be placed between the translation member 218 and actuation member 220 without having to form a recess in the translation member. For example, a PEEK washer can be provided between the interface of the translation member 218 and actuation member 220.

Although the preceding discussions only discussed having a single fusion device 210 in the intervertebral space, it is contemplated that more than one fusion device 210 can be inserted in the intervertebral space. It is further contemplated that each fusion device 210 does not have to be finally installed in the fully expanded state. Rather, depending on the location of the fusion device 210 in the intervertebral disc space, the height of the fusion device 210 may vary from unexpanded to fully expanded.

Trial Member

In some embodiments, the fusion devices 210 can be put into place with the assistance of a novel expandable trial member. The expandable trial member can be used prior to inserting an expandable fusion device in between vertebral bodies to obtain an accurate size measurement for the fusion device. The expandable trial member can help a user determine a fusion device of an appropriate size to use in a vertebra. Advantageously, the novel expandable trial member disclosed herein is configured such that the amount of distraction force applied to the trial member is linear and constant over its entire expansion range.

Figure 45:
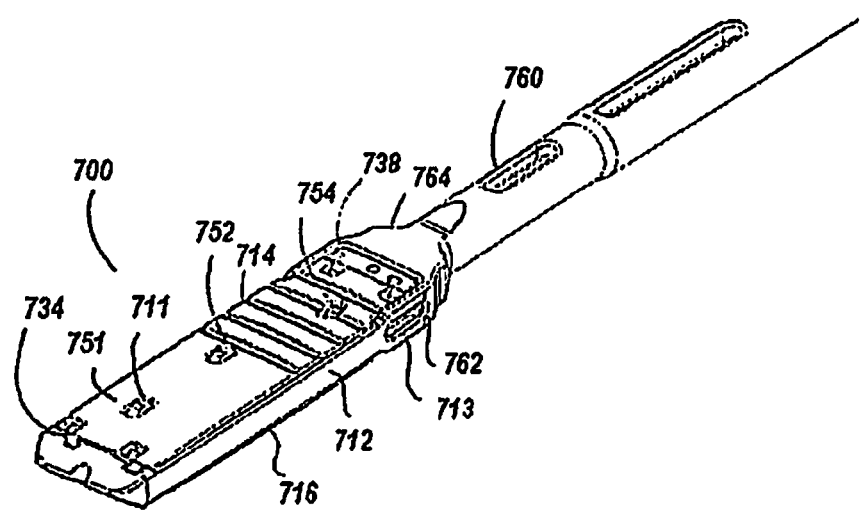
FIG. 45 is a perspective view of a trial member in a non-expanded configuration.
Figure 46:
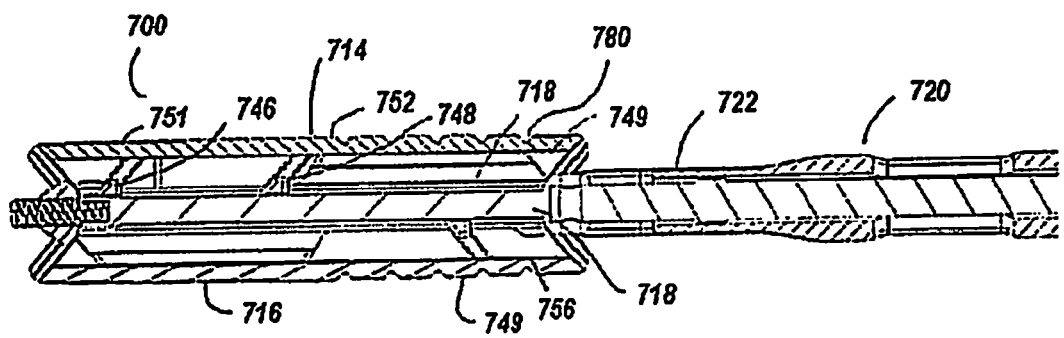
FIG. 46 is a side cross-sectional view of the trial member of FIG. 45 in an expanded configuration.
Figure 47:
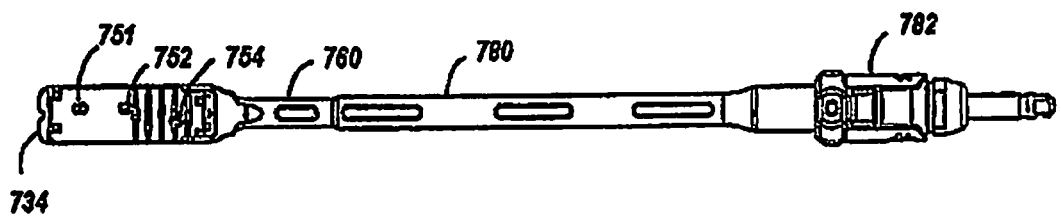
FIG. 47 is a top view of the trial member.
Figure 48:
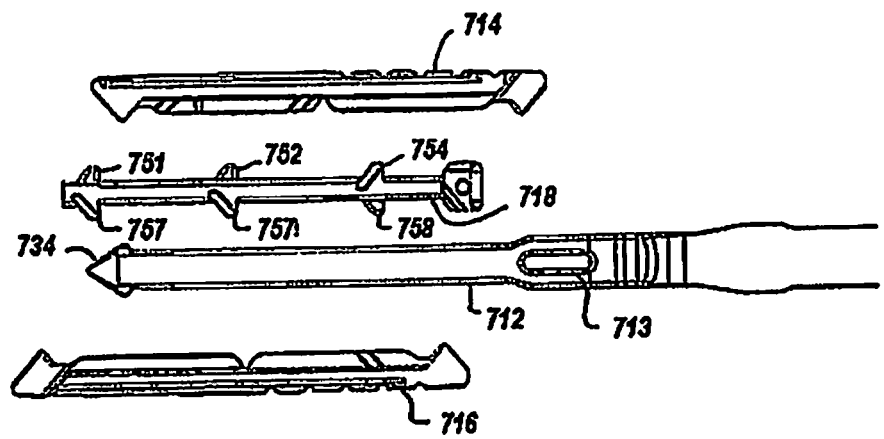
FIG. 48 is an exploded view of the trial member.

FIGS. 45-48 show different perspectives of an expandable trial member according to some embodiments. FIG. 45 illustrates a perspective view of the trial member in a non-expanded configuration. FIG. 46 illustrates a side cross-sectional view of the trial member in an expanded configuration. FIG. 47 illustrates a top view of the trial member. FIG. 48 shows an exploded view of the trial member.

As shown in the figures, the expandable trial member 700 comprises a body portion 712, an upper endplate 714, a lower endplate 716, a translation member 718 and an actuation member 720. The trial member 700 is configured such that when the actuation member 720 (shown in FIG. 46) is pulled in a backward or proximal direction toward a handle portion 782 (shown in FIG. 47), inner shaft or rod member 722 (shown in FIG. 46) will push forward and cause inner ramped surfaces of the translation member 718 to translate relative to inner angled grooves cut into the upper endplate 714 and/or lower endplate 716, thereby causing expansion of the trial member 700. When the actuation member 720 is pushed in a forward or distal direction away from the handle portion 782, the trial member 700 can collapse. In other embodiments, distal movement of the actuation member 720 can result in expansion of the expandable trial member, while proximal movement of the actuation member 720 can result in collapse of the trial member. The configuration of the trial member 700 thus allows pushing and pulling of the actuation member 720 to actuate the shaft or inner rod 722, thereby causing expansion or contraction of the trial member 700. Advantageously, because movement along the ramped surfaces of the upper endplate 714 and lower endplate 716 cause expansion or contraction, the amount of distraction force is linear over the entire expansion range of the trial member 700.

The expandable trial member 700 includes an upper endplate 714 and a lower endplate 716. As shown best in FIG. 46, both the upper endplate 714 and lower endplate 716 can include one or more surface grooves 780. While the trial member 700 need not remain over an extended period of time within a vertebra, the surface grooves 780 advantageously help to retain the trial member 700 within a vertebra during its operational use.

A body portion 712 can be placed in between the upper endplate 714 and lower endplate 716. The body portion 712 can include a sloped or chamfered anterior portion 734 (shown in FIG. 45) that assists in distraction of vertebral bodies.

Within the body portion 712, the translation member 718 can be received therein. As shown best in FIG. 48, the translation member 718 includes a plurality of upper ramped surfaces 751, 752 and 754 and a plurality of lower ramped surfaces 756, 757 and 758. As shown in FIG. 45, the upper and lower endplates 714 and 716 can include one or more holes 711 that accommodate the upper and lower ramped surfaces when the trial member 700 is in a closed configuration. The upper ramped surfaces and lower ramped surfaces are configured to slidably mate with corresponding grooves (such as upper grooves 746 and 748 and lower groove 749 shown in FIG. 46). When the actuation member 720 is pulled distally, the upper ramped surfaces slide downwardly through the grooves and the lower ramped surfaces slide upwardly through the grooves, thereby causing the expandable trial member 700 to expand from its closed configuration, shown in FIG. 45, to an expanded configuration, shown in FIG. 46.

In some embodiments, the body portion 712 can include a pair of side slots 713, as shown in FIG. 45. The side slots 713 are configured to each receive a side stabilization member 762. In some embodiments, the stabilization members 762 comprise stabilizer screws that contact the translation member 718. Advantageously, the stabilization members 762 help keep the translation member 718 centered inside the body portion 712 to prevent twisting as it translates forward and backwards.

In some embodiments, the trial member 700 is configured to expand to have a trial height that is at least fifty percent higher than a height of the trial member 700 in its closed configuration. In other embodiments, the trial member 700 is configured to expand to have a trial height that is at least two times the height of the trial member 700 in its closed configuration. By having a trial member 700 with a wide variety of expansion configurations, a user can advantageously choose a properly sized fusion implant to accommodate a number of different patients of different sizes.

FIGS. 51-55 show different views of some embodiments of a proximal portion 750 of a trial member 700. In some embodiments, the trial member 700 can be a single piece that extends from a proximal end to a distal end. In other embodiments, which are reflected in FIGS. 51-55, the proximal portion 750 can comprise a removable handle portion 782 that is configured to operably attach to a body of the trial member 700. Advantageously, by providing a removable handle portion 782, this helps to facilitate easier cleaning of the trial member 700. The proximal portion 750 is configured to assist in movement of the inner shaft 722 of the trial member, thereby causing expansion and contraction of the trial member upper and lower endplates. In addition, the proximal portion 750 can comprise a novel locking member that operably mates the proximal portion 750 to the inner shaft 722, thereby allowing the inner shaft 722 to be pulled back. Once the upper and lower endplates of the trial member are separated a desired distance, the trial member 700 can be removed, and an appropriately sized expandable implant can be inserted based on the separation distance between the upper and lower endplates.

Figure 51:
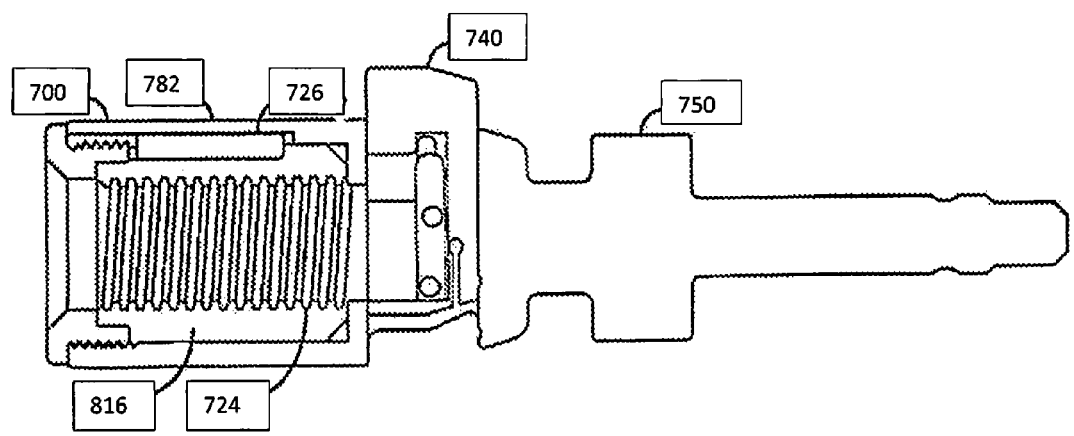
FIG. 51 is a side cross-sectional view of a proximal portion of a trial member in an unlocked configuration.

In the trial member 700 shown in FIG. 51, the removable proximal portion 750 is configured to operably attach to a body of the trial member (such as shown in FIG. 47). The proximal portion 750 is comprised of a handle 782 in the form of a housing member, a removable engagement insert 816, and a slidable locking member 740. The interior of the proximal portion 750 is configured to have a threaded insert 816 that mates with an exterior threaded surface 724 along the body of the trial member 700. As the proximal portion 750 is rotatably threaded onto the body portion, a surface of the slidable locking member 740 pushes against the inner shaft 722 (shown in FIG. 53 as within the exterior threaded surface 724), thereby causing expansion of the trial member endplates.

Figure 54:
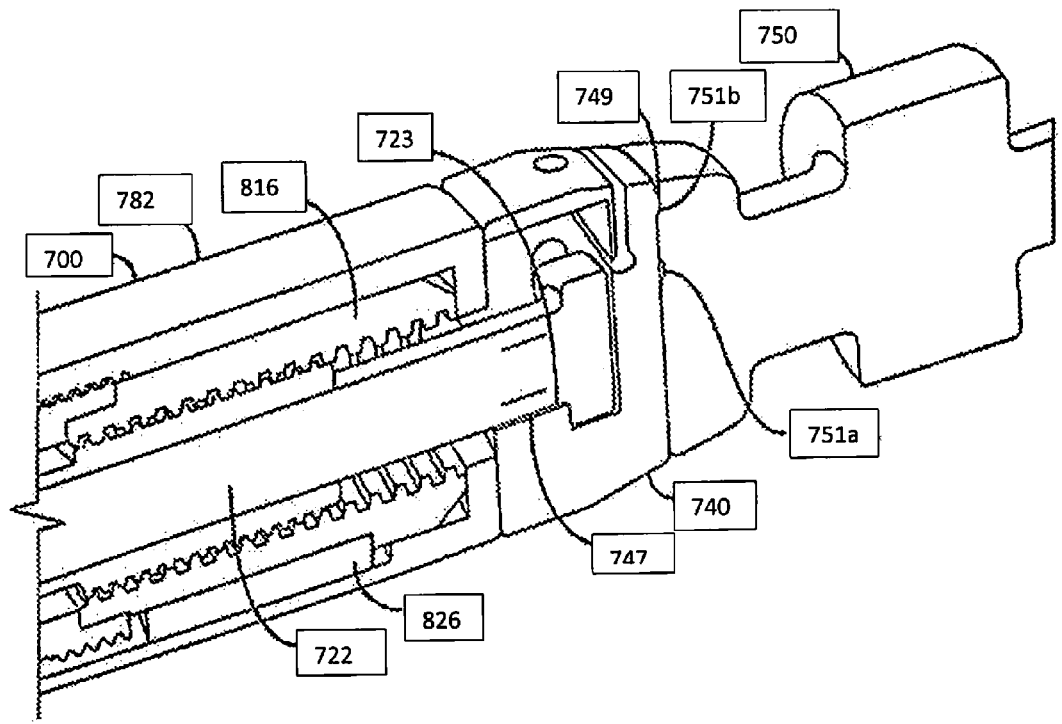
FIG. 54 is a perspective cross-sectional view of a proximal portion of a trial member in a locked configuration.
Figure 55:
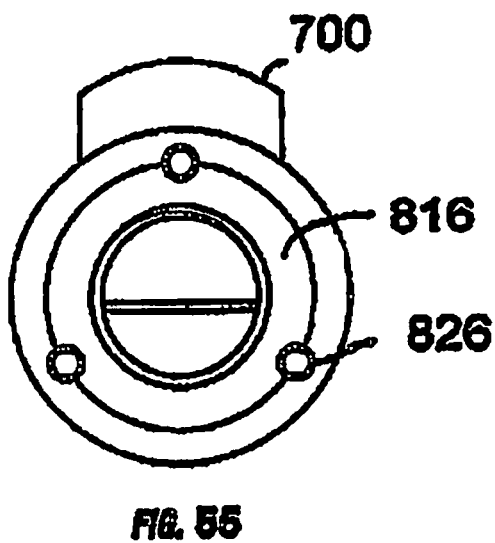
FIG. 55 is a front cross-sectional view of a proximal portion of a trial member.

The body of the handle portion 782 is configured to receive a threaded insert 816 therein. While in some embodiments, the threaded insert 816 is comprised of the same material as the exterior threaded surface 724 of the body, in other embodiments, the threaded insert 816 and threaded surface 724 are of different materials. For example, in some embodiments, the threaded insert 816 can be a polymer, such as PEEK, while the exterior threaded surface 724 can be a metal, such as stainless steel. One skilled in the art will appreciate that other materials can also be used. By providing a PEEK insert 816 that threads onto the metal threads, this advantageously reduces the friction between the two components, thereby reducing the amount of work that is absorbed by the two components and increasing the expansion forces transmitted to the endplates. In addition, the use of a threaded PEEK insert 816 on metal prevents thread galling over multiple uses under high loading. To prevent rotation of the insert 816, pin members 826 can be provided to contact the surface of the insert 816 along with the inner wall of the handle portion 782 (as shown in FIG. 54). As shown in FIG. 55, a plurality of pin members 826 can be provided that align with the longitudinal axis of the insert 816 to prevent rotation of the insert 816.

As the insert 816 of the removable proximal portion 750 is rotatably threaded onto the exterior threads of the body of the trial member, a surface of the slidable locking member 740 pushes against the inner shaft 722 of trial member, thereby causing expansion of the endplates. Reverse rotation of the threads of the insert 816 will result in contraction of the endplates. In some embodiments, the slidable locking member 740 can be moved from an unlocked to a locked configuration such that the inner shaft 722 is operably mated with the proximal portion 750 via the locking member 740. More details regarding the slidable locking member 740 are discussed below.

FIG. 39 illustrates the proximal portion 750 of the trial member with the slidable locking member 740 in an unlocked configuration, while FIG. 54 illustrates the proximal portion 750 of the trial member with the slidable locking member 740 in a locked configuration. In the unlocked configuration, the proximal portion 750 is able to translate along the body of the trial member, thereby pushing on the inner shaft 722 and causing expansion of the trial member endplates. In the locked configuration, the proximal portion 750 is operably mated to the inner shaft 722, thereby allowing the inner shaft 722 to be pulled back via the proximal portion 750 in situ.

Figure 52:
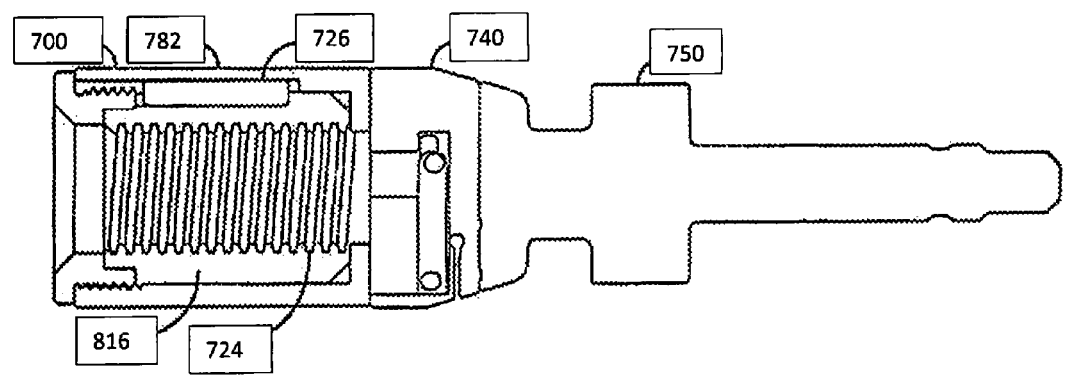
FIG. 52 is a side cross-sectional view of a proximal portion of a trial member in a locked configuration.
Figure 53:
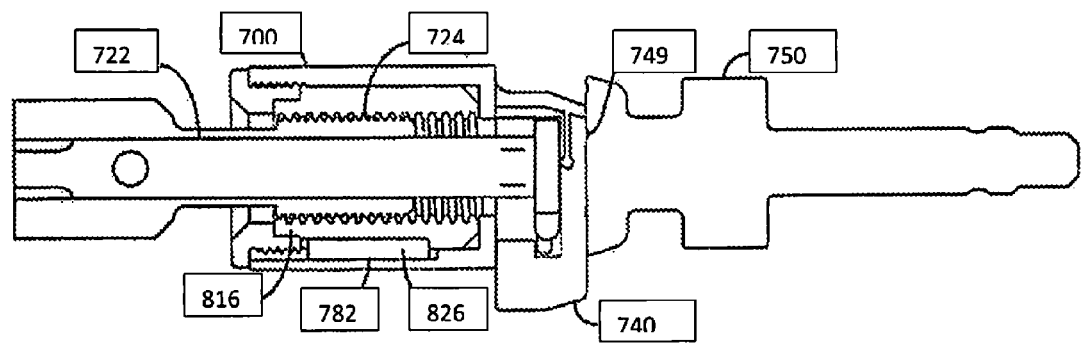
FIG. 53 is an alternate side cross-sectional view of a proximal portion of a trial member in a locked configuration.

The slidable locking member 7540 comprises an insert attached to the proximal portion 750 of the trial member. In some embodiments, the locking member 740 comprises a J-shaped or hook-shaped body that is configured to slide up and down in order to provide unlocked and locked configurations, as shown in FIGS. 51 and 52 respectively. The body of the locking member 740 can include a nub 749 (identified in FIGS. 53 and 54) that can be received in a snap-fit into corresponding grooves 751a and 751b formed in the proximal portion 750. When the nub 749 is in groove 751a, the locking member 740 is in an unlocked configuration. When the nub 749 is in groove 751b, the locking member 740 is in a locked configuration.

As shown in FIG. 54, the hook-shaped body of the locking member 740 also includes a mating end 747 that can be received in a complementary mating portion 723 of the inner shaft 722. When the mating end 747 is received in the mating portion 723 of the inner shaft 722, this advantageously mates the proximal portion 750 to the inner shaft 722, thereby allowing the inner shaft 722 to be pulled back in situ if desired.

In some embodiments, the locking member 740 is of the same material as surfaces of the proximal portion 750 and/or the inner shaft 722. In other embodiments, the locking member 740 is of a different material from surfaces of the proximal portion 750 and/or the inner shaft 722. For example, the locking member 740 can be formed of a polymer such as PEEK, while an adjacent surface of the proximal portion 750 is a metal such as stainless steel. By providing a locking member 740 that is of a lubricious material such as PEEK, this advantageously reduces the friction between the locking member 740 and adjacent surfaces, thereby resulting in less galling between adjacent surfaces.

Various methods are provided for utilizing fusion devices and trial members are provided. In some embodiments, a cavity is formed in a vertebral space between two vertebrae. An expandable trial member including a first endplate, a second endplate, a translation member with ramped surfaces, a body portion and an actuation member can be provided. In an unexpanded form, the trial member can be introduced into the vertebral space. Once in the vertebral space, the actuation member can be rotated, thereby causing expansion of the first endplate and second endplate via motion of the translation member. With the trial member in the vertebral space, an assessment can be made as to the proper size of an expandable fusion device.

Once the trial member is removed, an expandable fusion device comprising a first endplate, a second endplate, a translation member with ramped surfaces, a body portion and an actuation member can be provided. Optionally, the trial member can include an interference nut that is attached to a rear section of the body portion, one or more front or side stabilization members, a flange, a blocking nut, or combinations thereof. The expandable fusion device can be inserted into the vertebral space in an unexpanded form. Once in the vertebral space, the actuation member of the fusion device can be rotated, thereby causing expansion of the first endplate and second endplate via motion of the translation member. Once in its expanded form, the fusion device is kept in place and can remain in the vertebral space for an extended period of time.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An intervertebral implant comprising:
a first endplate;
a second endplate;
a translation member received between the first endplate and the second endplate, the translation member including a first angled surface configured to engage a contact surface of the first endplate,
two stabilization members extending from the translation member, and a body having a first side wall portion extending along a longitudinal axis of the implant and a second side wall portion extending along a longitudinal axis of the implant, each side wall portion having a slot, wherein each slot is configured to receive a portion of a respective one of said stabilization members,
wherein movement of the translation member causes the first angled surface to push against the contact surface of the first endplate thereby causing outward expansion of the first endplate and second endplate,
wherein the translation member includes an opening for receiving an actuation member, the actuation member being configured not to extend beyond the first angled surface of the translation member when the first and second endplates are in an unexpanded state.

2. The implant of claim 1, wherein a through hole extends through the first endplate, the translation member and the second endplate.

3. The implant of claim 2, wherein the actuation member comprises a threaded member.

4. The implant of claim 2, wherein rotation of the actuation member causes translational movement of the translation member.

5. The implant of claim 1, wherein the first endplate includes an angled surface.

6. The implant of claim 1, wherein the translation member comprises a second angled surface connected to the first angled surface by a bridge portion.

7. The implant of claim 1, wherein the first and second endplates are coupled to the translation member by dovetail connections.

8. An intervertebral implant comprising:
a first endplate having an upper side and a lower side, wherein the first endplate includes a first opening;
a second endplate having an upper side and a lower side, wherein the second endplate includes a second opening;
a translation member positioned between the first endplate and the second endplate, the translation member including a first angled surface, a second angled surface, a third angled surface and a fourth angled surface, the first and second angled surface configured to engage a first and second surface of the first endplate and the third and fourth angled surface configured to engage a third and fourth surface of the second endplate,
two stabilization members extending from the translation member, and a body having a first side wall portion extending along a longitudinal axis of the implant and a second side wall portion extending along a longitudinal axis of the implant, each side wall portion having a slot, wherein each slot is configured to receive a portion of a respective one of said stabilization members,
wherein the first and second angled surfaces are spaced apart along the longitudinal axis of the implant,
wherein the first angled surface is configured with a first slope angle and the second angled surface is configured with a second slope angle,
wherein the first slope angle and the second slope angle are not equal to one another.

9. The implant of claim 8, wherein movement of the translation member in a first direction causes the first and second angled surface to push against the first and second surface of the first endplate and the third and fourth angled surface to push against the third and fourth surface of the second endplate, thereby causing outward expansion of the first endplate and second endplate.

10. The implant of claim 9, wherein the translation member is coupled to the first and second endplates through dovetail connections.

11. The implant of claim 8, wherein the third and fourth angled surfaces of the translation member are configured with a first and second slope.

12. The implant of claim 11, wherein the first and second slopes of the third and fourth angled surfaces of the second endplate are not equal.

13. The implant of claim 11, wherein the first and second slopes of the third and fourth angled surfaces of the second endplate are equal.

14. The implant of claim 8, further comprising an actuation member engaged with the translation member.

15. An intervertebral implant comprising:
a first endplate having an upper side and a lower side;
a second endplate having an upper side and a lower side;
a translation member including at least two first angled surfaces configured to engage a first ramped surface and a second ramped surface of the first endplate and at least two second angled surfaces configured to engage a third ramped surface and a fourth ramped surface of the second endplate,
two stabilization members extending from the translation member, and a body having a first side wall portion extending along a longitudinal axis of the implant and a second side wall portion extending along a longitudinal axis of the implant, each side wall portion having a slot, wherein each slot is configured to receive a portion of a respective one of said stabilization members,
wherein the at least two first angled surfaces are sloped generally in the same direction,
wherein the at least two second angled surfaces are sloped generally in the same direction,
wherein the first ramped surface and the second ramped surface of the first endplate are configured with a first slope and a second slope, wherein the first slope and the second slope are spaced apart along the longitudinal axis of the implant and sloped in the same direction.

16. The intervertebral implant of claim 15, wherein the first slope and the second slope of the first and second ramped surface of the first endplate are different.

17. The intervertebral implant of claim 15, wherein the third ramped surface and the fourth ramped surface are spaced apart along the longitudinal axis of the implant and configured with a first slope and a second slope, the first and second slope of the third and fourth ramped surface are sloped in the same direction.

18. The intervertebral implant of claim 17, wherein the first slope and the second slope of the third and fourth ramped surfaces of the second endplate are different.

19. The intervertebral implant of claim 15, wherein movement of the translation member in a first direction causes the first angled surface to push against the first ramped surface of the first endplate and the second angled surface to push against at least the third ramped surface of the second endplate, causing outward expansion of the first endplate and second endplate.

20. The intervertebral implant of claim 15, wherein the translation member includes an opening for receiving an actuation member, the actuation member being configured not to extend beyond the first angled surface of the translation member when the first and second endplates are in an unexpanded state.

* * * * *